United States Patent
Allesen-Holm

(10) Patent No.: US 11,060,049 B2
(45) Date of Patent: Jul. 13, 2021

(54) USE OF POLYPEPTIDE

(71) Applicant: Novozymes A/S, Bagsvaerd (DK)

(72) Inventor: Marie Allesen-Holm, Hillerod (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/311,888

(22) PCT Filed: May 28, 2015

(86) PCT No.: PCT/EP2015/061829
§ 371 (c)(1),
(2) Date: Nov. 17, 2016

(87) PCT Pub. No.: WO2015/181287
PCT Pub. Date: Dec. 3, 2015

(65) Prior Publication Data
US 2017/0081617 A1    Mar. 23, 2017

(30) Foreign Application Priority Data

May 28, 2014 (EP) .................................... 14170347
Jun. 16, 2014 (EP) .................................... 14172549

(51) Int. Cl.
*C11D 3/386* (2006.01)
*C11D 17/04* (2006.01)
*C12N 9/22* (2006.01)

(52) U.S. Cl.
CPC ........ *C11D 3/38636* (2013.01); *C11D 17/049* (2013.01); *C12Y 301/00* (2013.01); *C12N 9/22* (2013.01)

(58) Field of Classification Search
None
See application file for complete search history.

(56) References Cited

U.S. PATENT DOCUMENTS

2016/0075976 A1 * 3/2016 Andersen ................. C12N 9/98
435/264

FOREIGN PATENT DOCUMENTS

| DE | 10304331 | * | 8/2004 |
| WO | 2011/098579 A1 | | 8/2011 |
| WO | 2013/175172 A1 | | 11/2013 |
| WO | 2014/087011 A1 | | 6/2014 |

* cited by examiner

*Primary Examiner* — Jennifer E Graser
(74) *Attorney, Agent, or Firm* — Elias Lambiris

(57) ABSTRACT

The present invention concerns the use of a polypeptide having deoxyribonuclease (DNase) activity for preventing, reducing or removing static electricity from an item; a composition comprising such polypeptide; a method for reducing or removing static electricity from an item; and a wipe for such use.

13 Claims, No Drawings
Specification includes a Sequence Listing.

USE OF POLYPEPTIDE

CROSS-REFERENCE TO RELATED APPLICATIONS

This application is a 35 U.S.C. 371 national application of international application no. PCT/EP2015/061829 filed May 28, 2015, which claims priority or the benefit under 35 U.S.C. 119 of European application nos. 14170347.0 and 14172549.9 filed May 28, 2014 and Jun. 16, 2014, respectively. The content of each application is fully incorporated herein by reference.

REFERENCE TO A SEQUENCE LISTING

This application contains a Sequence Listing in computer readable form, which is incorporated herein by reference.

FIELD OF THE INVENTION

The present invention concerns the use of a polypeptide having deoxyribonuclease (DNase) activity for reducing or removing static electricity from an item; a composition comprising such polypeptide; a wipe comprising the polypeptide; and a method for reducing or removing static electricity from an item.

BACKGROUND OF INVENTION

Static electricity is an imbalance of electric charges within or on the surface of a material. The charge remains until it is able to move away by means of an electric current or electrical discharge. A static electric charge is created whenever two surfaces contact and separate, and at least one of the surfaces has a high resistance to electrical current. The effects of static electricity are familiar to most people because people can feel, hear, and even see the spark as the excess charge is neutralized when brought close to a large electrical conductor (for example, a path to ground), or a region with an excess charge of the opposite polarity (positive or negative). The familiar phenomenon of a static shock, more specifically, an electrostatic discharge is caused by the neutralization of charge.

Static electricity can be a problem in many places where the static electricity builds up over a period of time, for example when laundering items made of synthetic fibers, such as polyester, polyamide, nylon, elastane (Spandex, Lycra), polyamide, fleece (Polyethylene terephthalate (PET)) or other synthetic fibers or mixtures thereof. After laundering the garment, due to static electricity, tend to adhere to the body and attract dust. The clothes can even transfer the static electricity to the hair, e.g. when a T-shirt is pulled over the head. This is very unpleasant for the person wearing the static electrical clothes even more because the static electricity does not discharge easy. Softeners are often used during the rinsing of laundry, however, the use of softeners does not prevent the problem. Further, it is recommended not to use softeners for sportswear or outdoor clothing with breathable membranes such as Goretex®.

As the use of synthetic materials is becoming more and more popular for wearing (sportswear, outdoor clothing, everyday clothing) or for cleaning (dishcloth, kitchen cloth, dustcloth or the like) static electricity build up during use and during washing is an increasing problem.

Other places where static electricity causes a problem can be all other places where a continuous contact/separation occur and which at the same time are soiled with DNA-containing material, e.g. floors, conveyor belts or other fitness equipment, production equipment, production plants, upholstery in cars, hair, glasses, sunglasses, touch screens on smartphones and tablets.

International patent application WO 2011/098579 concerns bacterial deoxyribonuclease compounds and methods for biofilm disruption and prevention.

SUMMARY OF THE INVENTION

The present invention concerns the use of a polypeptide having DNase activity for reducing or removing static electricity from an item. The invention further concerns a composition for reducing or removing static electricity, which composition comprises a polypeptide having deoxyribonuclease (DNase) activity and an antistatic agent.

Further is claimed a method for reducing or removing the static electricity of an item comprising the steps of:
a. Contacting an item with a composition comprising a polypeptide having DNase activity; and
b. Optionally rinsing the item,
wherein the item is a textile or a hard surface.

Also claimed is a wipe comprising a polypeptide having DNase activity.

Definitions

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

An antistatic agent is a compound used for treatment of materials or their surfaces in order to reduce or eliminate buildup of static electricity. Its role is to make the surface or the material itself slightly conductive, either by being conductive itself, or by absorbing moisture from the air, so some humectants can be used. The molecules of an antistatic agent often have both hydrophilic and hydrophobic areas, similar to those of a surfactant; the hydrophobic side interacts with the surface of the material, while the hydrophilic side interacts with the air moisture and binds the water molecules.

Bacterial: In the context of the present invention, the term "bacterial" in relation to polypeptide (such as an enzyme, e.g. a DNAse) refers to a polypeptide encoded by and thus directly derivable from the genome of a bacteria, where such bacteria has not been genetically modified to encode said polypeptide, e.g. by introducing the encoding sequence in the genome by recombinant DNA technology. In the context of the present invention, the term "bacterial DNAse" or "polypeptide having DNAse activity obtained from a bacterial source" or "polypeptide is of bacterial origin" thus refers to a DNAse encoded by and thus directly derivable from the genome of a bacterial species, where the bacterial species has not been subjected to a genetic modification introducing recombinant DNA encoding said DNAse. Thus, the nucleotide sequence encoding the bacterial polypeptide having DNAse activity is a sequence naturally in the genetic background of a bacterial species. The bacterial polypeptide having DNAse activity encoding by such sequence may also be referred to a wildtype DNAse (or parent DNAse). In a further aspect, the invention provides polypeptides having DNase activity, wherein said polypeptides are substantially homologous to a bacterial DNase. In the context of the present invention, the term "substantially homologous" denotes a polypeptide having DNase activity which is at least 80%, preferably at least 85%, more preferably at least 90%, more preferably at least 95%, even more preferably at least 96%, 97%, 98%, and most preferably at least 99% identical to the amino acid sequence of a selected bacterial DNase.

Biofilm: A biofilm is any group of microorganisms in which cells stick to each other or stick to a surface, such as a textile, dishware or hard surface or another kind of surface. These adherent cells are frequently embedded within a self-produced matrix of extracellular polymeric substance (EPS). Biofilm EPS is a polymeric conglomeration generally composed of extracellular DNA, proteins, and polysaccharides. Biofilms may form on living or non-living surfaces. The microbial cells growing in a biofilm are physiologically distinct from planktonic cells of the same organism, which, by contrast, are single-cells that may float or swim in a liquid medium.

Bacteria living in a biofilm usually have significantly different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community.

On laundry biofilm producing bacteria can be found among the following species: *Acinetobacter* sp., *Aeromicrobium* sp., *Brevundimonas* sp., *Microbacterium* sp., *Micrococcus luteus, Pseudomonas* sp., *Staphylococcus epidermidis*, and *Stenotrophomonas* sp. On hard surfaces biofilm producing bacteria can be found among the following species: *Acinetobacter* sp., *Aeromicrobium* sp., *Brevundimonas* sp., *Microbacterium* sp., *Micrococcus luteus, Pseudomonas* sp., *Staphylococcus epidermidis*, and *Stenotrophomonas* sp In one embodiment the biofilm producing strain is *Brevundimonas* sp. In one embodiment the biofilm producing strain is *Pseudomonas alcaliphila* or *Pseudomonas fluorescens.* cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Detergent components: the term "detergent components" is defined herein to mean the types of chemicals which can be used in detergent compositions. Examples of detergent components are alkalis, surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants and solubilizers.

Detergent Composition: the term "detergent composition" refers to compositions that find use in the removal of undesired compounds from items to be cleaned, such as textiles. The detergent composition may be used to e.g. clean textiles for both household cleaning and industrial cleaning.

The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; fabric fresheners; fabric softeners; and textile and laundry pre-spotters/pre-treatment). In addition to containing the enzyme of the invention, the detergent formulation may contain one or more additional enzymes (such as proteases, amylases, lipases, cutinases, cellulases, endoglucanases, xyloglucanases, pectinases, pectin lyases, xanthanases, peroxidaes, haloperoxygenases, catalases and mannanases, or any mixture thereof), and/or detergent adjunct ingredients such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

DNase (deoxyribonuclease): The term "DNase" means a polypeptide with DNase activity activity that catalyzes the hydrolytic cleavage of phosphodiester linkages in the DNA backbone, thus degrading DNA. For purposes of the present invention, DNase activity is determined according to the procedure described in the Assay I. In one aspect, the polypeptides of the present invention have at least 20%, e.g., at least 40%, at least 50%, at least 60%, at least 70%, at least 80%, at least 90%, at least 95%, or at least 100% of the DNase activity of the mature polypeptide of SEQ ID NO: 2. For purposes of the present invention, DNase activity is determined according to the procedure described in the Assay I. In one embodiment of the present invention, the DNAse activity of polypeptide having is at least 105%, e.g., at least 110%, at least 120%, at least 130%, at least 140%, at least 160%, at least 170%, at least 180%, or at least 200% with reference to the DNase activity of the mature polypeptide of SEQ ID NO: 2, a polypeptide comprising or consisting of the sequence set forth in SEQ ID NO: 3, a polypeptide comprising or consisting of the sequence set fort in SEQ ID NO: 5, a polypeptide comprising or consisting of the mature polypeptide of SEQ ID NO: 6, a polypeptide comprising or consisting of the mature polypeptide of SEQ ID NO: 7 or a polypeptide comprising or consisting of the mature polypeptide of SEQ ID NO: 8.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide or domain; wherein the fragment has DNase activity. In one aspect, a fragment contains at least 206 amino acid residues (e.g., amino acids 1 to 206 of SEQ ID NO: 2), at least 205 amino acid residues (e.g., amino acids 2 to 206 of SEQ ID NO: 2), or at least 204 amino acid residues (e.g., amino acids 3 to 206 of SEQ ID NO: 2). In one aspect, a fragment contains at least 139 amino acid residues (e.g., amino acids 50 to 188 of SEQ ID NO: 5), or at least 188 amino acid residues (e.g., amino acids 1 to 188 of SEQ ID NO: 5).

Fungal: In the context of the present invention the term "fungal" in relation to polypeptide (such as an enzyme, e.g. a DNAse) refers to a polypeptide encoded by and thus directly derivable from the genome of a fungus, where such fungus has not been genetically modified to encode said polypeptide, e.g. by introducing the encoding sequence in the genome by recombinant DNA technology. In the context of the present invention, the term "fungal DNAse" or "polypeptide having DNAse activity obtained from a fungal source" or "polypeptide is of fungal origin" thus refers to a DNAse encoded by and thus directly derivable from the genome of a fungal species, where the fungal species has not been subjected to a genetic modification introducing recombinant DNA encoding said DNAse. Thus, the nucleotide sequence encoding the fungal polypeptide having DNAse activity is a sequence naturally in the genetic background of a fungal species. The fungal polypeptide having DNAse activity encoding by such sequence may also be referred to a wildtype DNAse (or parent DNAse). In a further aspect, the invention provides polypeptides having DNase activity, wherein said polypeptides are substantially homologous to a fungal DNase. In the context of the present invention, the term "substantially homologous" denotes a polypeptide having DNase activity which is at least 80%, preferably at least 85%, more preferably at least 90%, more preferably at least 95%, even more preferably at least 96%, 97%, 98%, and most preferably at least 99% identical to the amino acid sequence of a selected fungal DNase.

Hard surface: The term "hard surface" is defined herein as a surface that does not absorb water. In particular, the term "hard surface" does not encompass a textile or fabric.

Items having a hard surface and falling within the intended meaning of the term therefore include household surfaces, surfaces in hospitals/institutions and outdoor surfaces such as floors, walls, roofs etc. as well as surfaces of hard objects such as cars (car wash) tables and other furniture, and dishware. Dishware includes but is not limited to crockery such as plates, cups, glasses, bowls, cutlery such as spoons, knives, forks, serving utensils, and other items made from ceramics, plastics, metals, china, glass and acrylics, etc.

Hard surface detergent composition: The term "hard surface detergent composition" refers to compositions comprising detergent components, which composition is suitable and intended for cleaning hard surfaces areas. The present invention is not restricted to any particular type of hard surface cleaning composition or any particular detergent.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

Laundering: The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

By the term "malodor" is meant an odor which is not desired on clean items. The cleaned item should smell fresh and clean without malodors adhering to the item. One example of malodor is compounds with an unpleasant smell, which smell may be produced by microorganisms. Another example is unpleasant smells can be sweat or body odor adhered to an item which has been in contact with human or animal. Another example of malodor can be the odor from spices, herbs or perfumes which sticks to items for example curry or other exotic spices which smells strongly. One way of testing for the presence of malodor on an item is by using Assay II.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 206 of SEQ ID NO: 2 and amino acids −37 to −16 of SEQ ID NO: 2 are a signal peptide and amino acids −15 to −1 of SEQ ID NO: 2 are a propeptide. In one aspect, the mature polypeptide is amino acids 1 to 188 of SEQ ID NO: 5 and amino acids −17 to −1 of SEQ ID NO: 2 are a signal peptide. In one aspect, the mature polypeptide is amino acids 1 to 110 of SEQ ID NO: 6, the mature polypeptide is amino acids 1 to 109 of SEQ ID NO: 7 or the mature polypeptide is amino acids 1 to 206 of SEQ ID NO: 8. It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide. In one aspect, a mature polypeptides contains up to 206 amino acid residues and of SEQ ID NO: 2, SEQ ID NO: 3 or SEQ ID NO: 8 (e.g., amino acids 1 to 206 of SEQ ID NO: 2), or up to 204 amino acid residues (e.g., amino acids 3 to 206 of SEQ ID NO: 2).

Mature polypeptide coding sequence: The term "mature polypeptide coding sequence" means a polynucleotide that encodes a mature polypeptide having DNase activity. In one aspect, the mature polypeptide coding sequence is join nucleotides 1 to 242, 309 to 494, 556 to 714 and 766 to 907 of SEQ ID NO: 1. In one aspect, the mature polypeptide coding sequence is nucleotides 52 to 864 of SEQ ID NO: 4, where three introns are predicted in the sequence in amino acids in position 76-164, 289-362 and 520-615 of SEQ ID NO: 4. A secretion signal is present at amino acids in positions 1-51 of SEQ ID NO: 4.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

The term "Static electricity" means an imbalance of electric charges within or on the surface of a material or item. The charge remains until it is able to move away by means of an electric current or electrical discharge. A static electric charge can create whenever two surfaces contact and separate, and at least one of the surfaces has a high resistance to electrical current, or the static electric charge can create when DNA is present on a surface. The combination of DNA present on a surface and its contact and separating from another surface may also result in built up of static electricity within/on the surface. The effects of static electricity are familiar to most people because people can feel, hear, and even see the spark as the excess charge is neutralized when brought close to a large electrical conductor (for example, a path to ground), or a region with an excess charge of the opposite polarity (positive or negative). The removal of static electricity is demonstrated in example 1.

Sequence identity: The relatedness between two amino acid sequences or between two nucleotide sequences is described by the parameter "sequence identity". For purposes of the present invention, the sequence identity between two amino acid sequences may be determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences may be determined using the Needleman-Wunsch algorithm (Needleman and Wunsch, 1970, supra) as implemented in the Needle program of the EMBOSS package (EM-BOSS: The European Molecular Biology Open Software Suite, Rice et al., 2000, supra), prefer-ably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of
Alignment−Total Number of Gaps in Alignment).

Stringency Conditions:

The term "very low stringency conditions" means for probes of at least 100 nucleotides in length, prehybridization and hybridization at 42° C. in 5×SSPE, 0.3% SDS, 200 micrograms/m sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/m sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/m sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having DNase activity. In one aspect, a subsequence contains at least 796 nucleotides (e.g., nucleotides 112 to 907 of SEQ ID NO: 1), at least 793 nucleotides (e.g., nucleotides 115 to 907 of SEQ ID NO: 1), or at least 790 nucleotides (e.g., nucleotides 118 to 907 of SEQ ID NO: 1). In one aspect, a subsequence contains at least 587 nucleotides (e.g., nucleotides 278 to 864 of SEQ ID NO: 4), at least 650 nucleotides (e.g., nucleotides 215 to 864 of SEQ ID NO: 4), or at least 816 nucleotides (e.g., nucleotides 52 to 864 of SEQ ID NO: 4).

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, cellulose acetate fibers (tricell), lyocell or blends thereof. The textile or fabric may also be non-cellulose based such as natural polyamides including wool, camel, cashmere, mohair, rabbit and silk or synthetic polymers such as nylon, aramid, polyester, acrylic, polypropylene and spandex/elastane, or blends thereof as well as blends of cellulose based and non-cellulose based fibers. Examples of blends are blends of cotton and/or rayon/viscose with one or more companion material such as wool, synthetic fiber (e.g. polyamide fiber, acrylic fiber, polyester fiber, polyvinyl chloride fiber, polyurethane fiber, polyurea fiber, aramid fiber), and/or cellulose-containing fiber (e.g. rayon/viscose, ramie, flax/linen, jute, cellulose acetate fiber, lyocell). The textile can also be made of microfiber or microfiber, which is synthetic fiber made from polyesters, polyamides (e.g., nylon, Kevlar, Nomex, trogamide), or a conjugation of polyester, polyamide, and polypropylene (Prolen). Fabric may be conventional washable laundry, for example stained household laundry. When the term fabric or garment is used it is intended to include the broader term textiles as well.

Variant: The term "variant" means a polypeptide having same activity as the parent enzyme comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. In the context of the present invention, a variant of an identified DNAse has the enzymatic activity of the parent, i.e. the capacity of catalyzing the hydrolytic cleavage of phosphodiester linkages in the DNA backbone (deoxyribonuclease activity). In one embodiment, the deoxyribonuclease activity of the variant is increased with reference to the parent DNAse, e.g. the mature polypeptide of SEQ ID NO: 2.

Wash cycle: The term "wash cycle" is defined herein as a washing operation wherein textiles are immersed in the wash liquor, mechanical action of some kind is applied to the textile in order to release stains and to facilitate flow of wash liquor in and out of the textile and finally the superfluous wash liquor is removed. After one or more wash cycles, the textile is generally rinsed and dried.

Wash liquor: The term "wash liquor" is intended to mean the solution or mixture of water and detergents optionally including enzymes used for laundrering textiles, for hard surface cleaning or for dishwashing.

Wipe: The term wipe means a towel or a towelette and is a small piece of paper or wipe material e.g. a textile. The wipe can be made of any kind of textile, such as non-woven textile. One example of textile is microfiber in the form of mats, knits or weaves for cleaning products. The shape, size, and combinations of synthetic fibers are selected for specific characteristics, including softness, toughness, absorption, water repellency, electrodynamics, and filtering capabilities.

Wet wipe: The term wet wipe means a wet towel, or a moist towelette and is a small moistened piece of paper or wipe material e.g. textile that often comes folded and individually wrapped for convenience. Wet wipes are used for cleaning purposes, like personal hygiene (baby wipes) or household cleaning. For example wet wipes can be used for wiping away fingerprints and greasy smudges on eyeglasses, sunglasses, goggles, cell/smartphone screens, computer/laptop screens and more.

DETAILED DESCRIPTION OF THE INVENTION

The inventor has surprisingly found that polypeptides having deoxyribonuclease (DNase) activity can be used for preventing, reducing or removing static electricity from items on which static electricity accumulate such as textile and hard surfaces. Synthetic textiles such as textiles made of polyester, polyamide, nylon, elastane, polyamide or fleece easily build up static electricity when worn or during laundering. It is believed that the build up of DNA on items increases the static electricity of the item. A textile which is static electric easily adheres to the hair or body and accumulates dust. This is inconvenient for the person wearing the textile. Static electricity on garment can be prevented, reduced or even completely removed by the use of polypeptides having deoxyribonuclease (DNase) activity. The use of DNase can impart to the item a reduced tendency to pick up and/or retain electrostatic charge and thereby the tendency to attract dirt is also reduced. The use of DNase can protect fabrics against acquiring static-electrical charge during machine drying subsequent to laundering.

Furthermore, walking on a floor or ground covered with DNA and specific material has also shown to accumulate static electricity for the person walking. For example some synthetic carpets, synthetic floors or even the belt of treadmills can accumulate static electricity so a person will experience a static shock when discharging. The use of a polypeptide having DNase activity can prevent, reduce or remove the accumulation of static electricity.

Touching a touchscreen of e.g. a smart phone or tablet deposits DNA on the screen. This increases the static electricity of the screen which thereby increases the amount of dirt attracted to the screen. The screen thus appears even dirtier. The use of a polypeptide having DNase activity can prevent, reduce or remove the accumulation of static electricity and thus also the accumulation of dirt/particles. The use of a polypeptide having DNase activity can prevent, reduce or remove the accumulation of static electricity.

The polypeptide having DNase activity can, for example, be sprayed onto the item accumulating static electricity. The static electricity built up during production and use of synthetic items can be reduced or removed by spraying such items with the polypeptide. Exemplary items include carpets, floors, bed sheets or linen.

Another way of preventing, reducing or removing static electricity is contacting the item with a liquid solution comprising a polypeptide having DNase activity. The item can be contacted with the liquid solution for example by immersing the item into the liquid solution. The liquid solution can be a wash liquor and the item may be washed at the same time. Or the liquid solution can be a softener for use when rinsing or drying an item. The softener can be used in the rinsing water or applied to a sheet, which is used during rinsing or drying. This embodiment of the invention is preferred for textiles such as laundry textiles which can be washed, rinsed or dryed at the same time as the static electricity is removed.

The wash liquor can also be used for washing floors or other hard surfaces which need anti-static treatment.

The liquid solution can also be an impregnation liquid which liquid prevents the item from building up static electricity. The liquid solution for impregnation may serve as detergent and anti-static solution at the same time. The polypeptide having DNase activity can also be coated or painted onto the item that needs anti-static treatment, such as floors or treadmills.

The invention further concerns a composition for preventing, reducing or removing static electricity, wherein the composition comprises a polypeptide having deoxyribonuclease (DNase) activity and an antistatic agent.

The composition can be a laundry detergent composition, a dish wash detergent composition, a composition for hard surface cleaning, a laundry softening composition or a composition for personal care.

In one embodiment, the composition is a laundry detergent composition, a dish wash detergent composition or a composition for hard surface cleaning.

In one embodiment, the composition is a laundry softening composition. The laundry softening composition can be applied to a textile, which may be used during washing, rinsing or drying the item.

The composition can further comprise surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, bacteriocides, fungicides and/or pigments.

The composition can comprise one or more enzymes selected from the group consisting of proteases, lipases, cutinases, amylases, carbohydrases, cellulases, pectinases, mannanases, arabinases, galactanases, xylanases and oxidases.

The composition may be a detergent composition suitable for laundering or hard surface cleaning.

The invention further concerns a liquid detergent composition comprising a surfactant and a detergent and a detergent builder in a total concentration of at least 3% by weight, and a detergent enzyme containing microcapsule, wherein the membrane of the microcapsule is produced by cross-linking of a polybranched polyamine having a molecular weight of more than 1 kDa. The inventors have found, that encapsulating enzymes in a microcapsule with a semipermeable membrane, and having a water activity inside these capsules (prior to addition to the liquid detergent) higher than in the liquid detergent, the capsules will undergo a (partly) collapse when added to the detergent (water is oozing out), thus leaving a more concentrated and more viscous enzyme containing interior in the capsules. The collapse of the membrane may also result in a reduced permeability. This can be further utilized by addition of stabilizers/polymers, especially ones that are not permeable through the membrane. The collapse and resulting increase in viscosity will reduce/hinder the diffusion of hostile components (e.g., surfactants or sequestrants) into the capsules, and thus increase the storage stability of the enzyme in the liquid detergent. Components in the liquid detergent that are sensitive to the enzyme (e.g., components that act as substrate for the enzyme) are also protected against degradation by the enzyme. During wash the liquid detergent is diluted by water, thus increasing the water activity. Water will now diffuse into the capsules (osmosis). The capsules will swell and the membrane will either become permeable to the enzyme so they can leave the capsules, or simply burst and in this way releasing the enzyme. The concept is very efficient in stabilizing the enzymes against hostile components in liquid detergent, and vice versa also protects enzyme sensitive components in the liquid detergent from enzymes.

Examples of detergent components which are sensitive to, and can be degraded by, enzymes include (relevant enzyme in parenthesis): xanthan gum (xanthanase), polymers with ester bonds (lipase), hydrogenated castor oil (lipase), perfume (lipase), methyl ester sulfonate surfactants (lipase), cellulose and cellulose derivatives (e.g. CMC) (cellulase), and dextrin and cyclodextrin (amylase).

Also sensitive detergent ingredients can be encapsulated, and thus stabilized, in the microcapsules. Sensitive detergent ingredients are prone to degradation during storage. Such detergent ingredients include bleaching compounds, bleach activators, perfumes, polymers, builder, surfactants, etc.

Generally, the microcapsules can be used to separate incompatible components/compounds in detergents.

Addition of the microcapsules to detergents can be used to influence the visual appearance of the detergent product, such as an opacifying effect (small microcapsules) or an effect of distinctly visible particles (large microcapsules). The microcapsules may also be colored.

The microcapsules can be used to reduce the enzyme dust levels during handling and processing of enzyme products.

Unless otherwise indicated, all percentages are indicated as percent by weight (% w/w) throughout the application.

Microcapsule: The microcapsules are typically produced by forming water droplets into a continuum that is non-miscible with water—i.e., typically by preparing a water-in-oil emulsion—and subsequently formation of the membrane by interfacial polymerization via addition of a cross-linking agent. After eventual curing the capsules can be harvested and further rinsed and formulated by methods known in the art. The capsule formulation is subsequently added to the detergent.

The payload, the major membrane constituents and eventual additional component that are to be encapsulated are found in the water phase. In the continuum is found components that stabilize the water droplets towards coalescence (emulsifiers, emulsion stabilizers, surfactants etc.) and the cross linking agent is also added via the continuum.

The emulsion can be prepared be any methods known in the art, e.g., by mechanical agitation, dripping processes, membrane emulsification, microfluidics, sonication etc. In some cases simple mixing of the phases automatically will result in an emulsion, often referred to as self-emulsification. Using methods resulting in a narrow size distribution is an advantage.

The cross-linking agent(s) is typically subsequently added to the emulsion, either directly or more typically by preparing a solution of the crosslinking agent in a solvent which is soluble in the continuous phase. The emulsion and cross-linking agent or solution hereof can be mixed by conventional methods used in the art, e.g., by simple mixing or by carefully controlling the flows of the emulsion and the cross-linking agent solution through an in-line mixer.

In some cases, curing of the capsules is needed to complete the membrane formation. Curing is often simple stirring of the capsules for some time to allow the interfacial polymerization reaction to end. In other cases the membrane formation can be stopped by addition of reaction quencher.

The capsules may be post modified, e.g., by reacting components onto the membrane to hinder or reduce flocculation of the particles in the detergent as described in WO 99/01534.

The produced capsules can be isolated or concentrated by methods known in the art, e.g., by filtration, centrifugation, distillation or decantation of the capsule dispersion.

The resulting capsules can be further formulated, e.g., by addition of surfactants to give the product the desired properties for storage, transport and later handling and addition to the detergent. Other microcapsule formulation agents include rheology modifiers, biocides (e.g., Proxel), acid/base for adjustment of pH (which will also adjust inside the microcapsules), and water for adjustment of water activity.

The capsule forming process may include the following steps:
  Preparation of the initial water and oil phase(s),
  Forming a water-in-oil emulsion,
  Membrane formation by interfacial polymerization,
  Optional post modification,
  Optional isolation and/or formulation,
  Addition to detergent.

The process can be either a batch process or a continuous or semi-continuous process.

A microcapsule according to the invention is a small aqueous sphere with a uniform membrane around it. The material inside the microcapsule is referred to as the core, internal phase, or fill, whereas the membrane is sometimes called a shell, coating, or wall. The microcapsules have diameters between 0.5 µm and 2 millimeters. Preferably, the mean diameter of the microcapsules is in the range of 1 µm to 1000 µm, more preferably in the range of 5 µm to 500 µm, even more preferably in the range of 10 µm to 500 µm, even more preferably in the range of 50 µm to 500 µm, and most preferably in the range of 50 µm to 200 µm. Alternatively, the diameter of the microcapsules is in the range of 0.5 µm to 30 µm; or in the range of 1 µm to 25 µm. The diameter of the microcapsule is measured in the oil phase after polymerization is complete. The diameter of the capsule may change depending on the water activity of the surrounding chemical environment.

Microencapsulation of enzymes, as used in the present invention, may be carried out by interfacial polymerization, wherein the two reactants in a polymerization reaction meet at an interface and react rapidly. The basis of this method is a reaction of a polyamine with an acid derivative, usually an acid halide, acting as a crosslinking agent. The polyamine is preferably substantially water-soluble (when in free base form). Under the right conditions, thin flexible membranes form rapidly at the interface. One way of carrying out the polymerization is to use an aqueous solution of the enzyme and the polyamine, which are emulsified with a non-aqueous solvent (and an emulsifier), and a solution containing the acid derivative is added. An alkaline agent may be present in the enzyme solution to neutralize the acid formed during the reaction. Polymer (polyamide) membranes form instantly at the interface of the emulsion droplets. The polymer membrane of the microcapsule is typically of a cationic nature, and thus bind/complex with compounds of an anionic nature.

The diameter of the microcapsules is determined by the size of the emulsion droplets, which is controlled, for example by the stirring rate.

Emulsion: An emulsion is a temporary or permanent dispersion of one liquid phase within a second liquid phase. The second liquid is generally referred to as the continuous phase. Surfactants are commonly used to aid in the formation and stabilization of emulsions. Not all surfactants are equally able to stabilize an emulsion. The type and amount of a surfactant needs to be selected for optimum emulsion utility especially with regard to preparation and physical stability of the emulsion, and stability during dilution and further processing. Physical stability refers to maintaining an emulsion in a dispersion form. Processes such as coalescence, aggregation, adsorption to container walls, sedimentation and creaming, are forms of physical instability, and should be avoided. Examples of suitable surfactants are described in WO 97/24177, page 19-21; and in WO 99/01534.

Emulsions can be further classified as either simple emulsions, wherein the dispersed liquid phase is a simple homogeneous liquid, or a more complex emulsion, wherein the dispersed liquid phase is a heterogeneous combination of liquid or solid phases, such as a double emulsion or a multiple-emulsion. For example, a water-in-oil double emulsion or multiple emulsion may be formed wherein the water phase itself further contains an emulsified oil phase; this type of emulsion may be specified as an oil-in-water-in-oil (o/w/o) emulsion. Alternatively, a water-in-oil emulsion may be formed wherein the water phase contains a dispersed solid phase often referred to as a suspension-emulsion. Other more complex emulsions can be described. Because of the inherent difficulty in describing such systems, the term emulsion is used to describe both simple and more complex emulsions without necessarily limiting the form of the emulsion or the type and number of phases present.

Polyamine: The rigidity/flexibility and permeability of the membrane is mainly influenced by the choice of polyamine. The polyamine according to the invention is a polybranched polyamine. Each branch, preferably ending with a primary amino group serves as a tethering point in the membrane network, thereby giving the favorable properties. A polybranched polyamine according to the present invention is a polyamine having more than two branching points and more than two reactive amino groups (capable of reacting with the crosslinking agent, i.e., primary and secondary amino groups). The polybranched polyamine is used as starting material when the emulsion is prepared—it is not formed in situ from other starting materials. To obtain the attractive properties, the polybranched structure of the polyamine must be present as starting material.

There is a close relation between number of branching points and number of primary amines, since primary amines will always be positioned at the end of a branch: A linear amine can only contain two primary amines. For each branching point hypothetically introduced in such a linear di-amine will allow one or more primary amine(s) to be introduced at the end of the introduced branch(es). In this context we understand the primary amino group as part of the branch, i.e., the endpoint of the branch. For example, we consider both tris(2-aminoethyl)amine and 1,2,3-propanetriamine as molecules having one branching point. For the invention the polyamine has at least four primary amines. Branching points can be introduced from an aliphatic hydrocarbon chain as in the previously stated examples or from unsaturated carbon bonds, such as in, e.g., 3,3'-diaminobenzidine, or from tertiary amino groups, such as in N,N,N',N'-tetrakis-(2-aminoethyl)ethylenediamine.

In addition to the number of branching points, we have found that the compactness of the reactive amino groups is of high importance. A substance such as, e.g., N,N,N',N'-tetrakis-(12-aminododecyl)ethylenediamine would not be suitable. Neither would a peptide or protein, such as an enzyme, be suitable for membrane formation. Thus, the polybranched polyamine is not a peptide or protein.

In an embodiment, the reactive amino groups constitute at least 15% of the molecular weight of the polybranched polyamine, such as more than 20%, or more than 25%. Preferably, the molecular weight of the polybranched polyamine is at least 1 kDa; more preferably, the molecular weight of the polybranched polyamine is at least 1.3 kDa.

In a preferred embodiment, the polybranched polyamine is a polyethyleneimine (PEI), and modifications thereof, having more than two branching points and more than two reactive amino groups; wherein the reactive amino groups constitute at least 15% of the molecular weight of the PEI, such as more than 20%, or more than 25%. Preferably, the molecular weight of the PEI is at least 1 kDa.

Combinations of different polybranched polyamines may be used for preparing the microcapsule according to the invention.

The advantageous properties (e.g., enzyme storage stability, reduced enzyme leakage, reduced in-flux of detergent ingredients) of the microcapsule may be improved by adding one or more small amines with a molecular weight of less than 1 kDa. The small amine is preferably substantially water-soluble (when in free base form) and can be a material such as ethylene diamine, hexamethylene diamine, hexane diamine, diethylene tetramine, ethylene tetramine, diamino benzene, piperazine, tetramethylene pentamine or, preferably, diethylene triamine (DETA). The small amines may be added in an amount of up to 50%, preferably up to 40%, up to 30%, up to 20%, up to 10%, or up to 5%, by weight of the total content of small amine and polybranched polyamine, when preparing the microcapsule.

Crosslinking agent: The crosslinking agent as used in the present invention is a molecule with at least two groups/sites capable of reacting with amines to form covalent bonds.

The crosslinking agent is preferably oil soluble and can be in the form of an acid anhydride or acid halide, preferably an acid chloride. For example, it can be adipoyl chloride, sebacoyl chloride, dodecanedioc acid chloride, phthaloyl chloride, terephthaloyl chloride, isophthaloyl chloride, or trimesoyl chloride; but preferably, the crosslinking agent is terephthaloyl chloride or trimesoyl chloride.

The invention further concerns a method for reducing or removing the static electricity of an item comprising the steps of:
a. Contacting an item with a composition according to the invention, a wipe according to the invention or to a liquid solution comprising a polypeptide having DNase activity; and
b. Optionally rinsing the item,
wherein the item is a textile or a hard surface.

In one embodiment of the invention, the method further comprises washing the item in or with the liquid solution.

By contacting an item with a composition or a liquid solution is meant contacting the item with the composition/solution for example by spraying, coating, immersing the item with the composition or the liquid solution. The item may be contacted with the item for a short period of time such as a 1-60 seconds or for a longer period of time such as 1-60 minutes or even longer such as 1-12 hours.

The liquid solution can further comprise antistatic agents, surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, bacteriocides, fungicides and/or pigments.

In one embodiment, the liquid solution further comprises one or more enzymes selected from the group consisting of proteases, lipases, cutinases, amylases, carbohydrases, cellulases, pectinases, mannanases, arabinases, galactanases, xylanases and oxidases.

The pH of the liquid solution is in the range of 1 to 11, such as in the range of 5.5 to 11, such as in the range of 7 to 9, in the range of 7 to 8 or in the range of 7 to 8.5.

The temperature of the liquid solution can be in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° C. to 30° C. In one embodiment the temperature of the liquid solution is 30° C.

In one embodiment, the item is rinsed after being contacted with to the liquid solution or the composition. The item can be rinsed with water or with water comprising a conditioner.

The DNase of the present invention may be present in a detergent composition in an amount corresponding to at least 0.002 mg of DNase protein, such as at least 0.004 mg of DNase protein, at least 0.006 mg of DNase protein, at least 0.008 mg of DNase protein, at least 0.01 mg of DNase protein, at least 0.1 mg of protein, preferably at least 1 mg of protein, more preferably at least 10 mg of protein, even more preferably at least 15 mg of protein, most preferably at least 20 mg of protein, and even most preferably at least 25 mg of protein. Thus, the detergent composition may comprise at least 0.00008% DNase protein, preferably at least 0.002%, 0.003%, 0.004%, 0.005%, 0.006%, 0.008%, 0.01%, 0.02%, 0.03%, 0.05%, 0.1%, 0.2%, 0.3%, 0.4%, 0.6%, 0.7%, 0.8%, 0.9% or 1.0% of DNase protein.

The invention further concerns a wipe for preventing, reducing or removing static electricity, which wipe comprises a polypeptide having DNase activity. The wipe can be impregnated or coated with the polypeptide having DNase activity. The wipe wipes away the dirt and soil from the item and the polypeptide having DNase activity further improves the cleaning as it removes DNA from the item and thereby cleans the item and in addition prevents, reduces and removes the static electricity on the item.

In one embodiment of the invention, the wipe is made of textile or paper. The textile can be selected from the group consisting of cotton, flax/linen, jute, ramie, sisal, coir, viscose/rayon, cellulose acetate fibers (tricell), lyocell, wool, camel, cashmere, mohair, rabbit and silk, nylon, aramid, polyester, acrylic, polypropylene, spandex/elastane, microfibre or blends thereof.

In one embodiment, the textile is a nonwoven textile or a spunlace textile, which can be made of microfiber.

The wipe can be a paper tissue selected from the group consisting of hygienic tissue paper, facial tissue paper, paper towels, towelettes, toilet tissue, table napkins, kitchen roll, handkerchief and glass cleaning tissue paper. The wipe can be a wet wipe packaged individually or in a package comprising two or more wet wipes. Such packages are easy to keep in a purse or bag, at home, school or work.

The wipe can be used for preventing, reducing or removing static electricity from surfaces such as surfaces on screens, touch screens, phones, tablets, cameras, lenses, jewelry, glasses, fitness equipment and CD's, The polypeptide having DNase activity can be of animal, vegetable or microbial origin. In one embodiment the polypeptide is of human origin. In one embodiment the polypeptide is obtained from plant material such as mung bean. In one embodiment the polypeptide is of bacterial or fungal origin.

A polypeptide of fungal origin may be selected from the group consisting of:
   a. a polypeptide having at least 60% sequence identity to the mature polypeptide of SEQ ID NO: 2, a polypeptide having at least 60% sequence identity to the mature polypeptide of SEQ ID NO: 3, a polypeptide having at least 60% sequence identity to the mature polypeptide of SEQ ID NO: 5 or a polypeptide having at least 60% sequence identity to the mature polypeptide of SEQ ID NO: 8
   b. a polypeptide encoded by a polynucleotide that hybridizes under low stringency conditions with
      i. the mature polypeptide coding sequence of SEQ ID NO: 1 or the mature polypeptide coding sequence of SEQ ID NO: 4
      ii. the cDNA sequence thereof, or
      iii. the full-length complement of (i) or (ii);
   c. a polypeptide encoded by a polynucleotide having at least 60% sequence identity to the mature polypeptide coding sequence of SEQ ID NO: 1 or the cDNA sequence thereof or a polypeptide encoded by a polynucleotide having at least 60% sequence identity to the mature polypeptide coding sequence of SEQ ID NO: 4 or the cDNA sequence thereof;
   d. a variant of the mature polypeptide of SEQ ID NO: 2 comprising a substitution, deletion, and/or insertion at one or more positions, a variant of the mature polypeptide of SEQ ID NO: 3 comprising a substitution, deletion, and/or insertion at one or more positions, a variant of the mature polypeptide of SEQ ID NO: 5 comprising a substitution, deletion, and/or insertion at one or more positions or a variant of the mature polypeptide of SEQ ID NO: 8 comprising a substitution, deletion, and/or insertion at one or more positions; and
   e. a fragment of the polypeptide of (a), (b), (c), or (d) that has DNase activity.

European patent application number 14164424.5 discloses in examples 1 to 3 how the polypeptide of SEQ ID NO: 2, SEQ ID NO: 3 and SEQ ID NO: 8 are produced. European patent application number 14164429.4 discloses in examples 1 to 2 how the polypeptide of SEQ ID NO: 5 is produced.

A polypeptide of bacterial origin may be selected from the group consisting of:
   a. a polypeptide having at least 60% sequence identity to the mature polypeptide of SEQ ID NO: 6 or a polypeptide having at least 60% sequence identity to the mature polypeptide of SEQ ID NO: 7;
   b. a variant of the mature polypeptide of SEQ ID NO: 6 comprising a substitution, deletion, and/or insertion at one or more positions or a variant of the mature polypeptide of SEQ ID NO: 7 comprising a substitution, deletion, and/or insertion at one or more positions; and
   c. a fragment of the polypeptide of (a) or (b) that has DNase activity;

The polypeptide can have at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, to the mature polypeptide of SEQ ID NO: 3, or to the mature polypeptide of SEQ ID NO: 5, or to the mature polypeptide of SEQ ID NO: 6 or to the mature polypeptide of SEQ ID NO: 7.

International patent application published under number WO2011098579 discloses in example 3 how to clone and express the polypeptide of SEQ ID NO: 6.

The polypeptide can comprise or consist of SEQ ID NO: 2 or the mature polypeptide of SEQ ID NO: 2, the polypeptide comprises or consists of SEQ ID NO: 3 or the mature polypeptide of SEQ ID NO: 3, the polypeptide comprises or consists of SEQ ID NO: 5 or the mature polypeptide of SEQ ID NO: 5, the polypeptide comprises or consists of SEQ ID NO: 6 or the mature polypeptide of SEQ ID NO: 6, the polypeptide comprises or consists of SEQ ID NO: 7 or the mature polypeptide of SEQ ID NO: 7 or the polypeptide comprises or consists of SEQ ID NO: 8 or the mature polypeptide of SEQ ID NO: 8.

The mature polypeptide can comprise amino acids 1 to 206 of SEQ ID NO: 2, amino acids 1 to 206 of SEQ ID NO: 3, amino acids 1 to 188 of SEQ ID NO: 5, amino acids 1 to 110 of SEQ ID NO: 6, amino acids 1 to 109 of SEQ ID NO: 7 or amino acids 1 to 206 of SEQ ID NO: 8.

The polypeptide can be a variant of the mature polypeptide of SEQ ID NO: 2, SEQ ID NO: 3, SEQ ID NO: 5, SEQ ID NO: 6, SEQ ID NO: 7 or SEQ ID NO: 8, wherein the variant comprises a substitution, deletion, and/or insertion at one or more positions or a variant of the mature polypeptide of SEQ ID NO: 2, SEQ ID NO: 3, SEQ ID NO: 5, SEQ ID NO: 6, SEQ ID NO: 7 or SEQ ID NO: 8 which comprises a substitution, deletion, and/or insertion at one or more positions.

The polypeptide can be a fragment of SEQ ID NO: 2, SEQ ID NO: 3, SEQ ID NO: 5, SEQ ID NO: 6, SEQ ID NO: 7 or SEQ ID NO: 8, wherein the fragment has DNase activity.

The polypeptide having DNase activity can be obtained from *Aspergillus*, for example from *Aspergillus oryzae*.

In an embodiment, the present invention relates to polypeptides having a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have DNase activity. In one aspect, the polypeptides differ by up to 10 amino acids, e.g., 1, 2, 3, 4, 5, 6, 7, 8, 9, or 10, from the mature polypeptide of SEQ ID NO: 2.

In an embodiment, the present invention relates to polypeptides having a sequence identity to the mature polypeptide of SEQ ID NO: 3 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have DNase activity. In one aspect, the polypeptides differ by up to 10 amino acids, e.g., 1, 2, 3, 4, 5, 6, 7, 8, 9, or 10, from the mature polypeptide of SEQ ID NO: 3.

In an embodiment, the present invention relates to polypeptides having a sequence identity to the mature polypeptide of SEQ ID NO: 8 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have DNase activity. In one aspect, the polypeptides differ by up to 10 amino acids, e.g., 1, 2, 3, 4, 5, 6, 7, 8, 9, or 10, from the mature polypeptide of SEQ ID NO: 8.

In another embodiment, the present invention relates to an polypeptide having DNase activity encoded by a polynucleotide having a sequence identity to the mature polypeptide coding sequence of SEQ ID NO: 2, SEQ ID NO: 5 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and wherein the polypeptide is used for preventing, reducing or removing static electricity from an item.

In an embodiment, the polypeptide has been isolated. A polypeptide of the present invention preferably comprises or consists of the amino acid sequence of SEQ ID NO: 2 or an allelic variant thereof; or is a fragment thereof having DNase activity. In another aspect, the polypeptide comprises or consists of the mature polypeptide of SEQ ID NO: 2. In another aspect, the polypeptide comprises or consists of amino acids 1 to 206 of SEQ ID NO: 2.

In an embodiment, the polypeptide has been isolated. A polypeptide of the present invention preferably comprises or consists of the amino acid sequence of SEQ ID NO: 3 or an allelic variant thereof; or is a fragment thereof having DNase activity. In another aspect, the polypeptide comprises or consists of the mature polypeptide of SEQ ID NO: 3. In another aspect, the polypeptide comprises or consists of amino acids 1 to 206 of SEQ ID NO: 3.

In an embodiment, the polypeptide has been isolated. A polypeptide of the present invention preferably comprises or consists of the amino acid sequence of SEQ ID NO: 8 or an allelic variant thereof; or is a fragment thereof having DNase activity. In another aspect, the polypeptide comprises or consists of the mature polypeptide of SEQ ID NO: 8. In another aspect, the polypeptide comprises or consists of amino acids 1 to 206 of SEQ ID NO: 8.

In another embodiment, the present invention relates to an isolated polypeptide having DNase activity encoded by a polynucleotide that hybridizes under low stringency conditions with (i) the mature polypeptide coding sequence of SEQ ID NO: 1, (ii) the cDNA sequence thereof, or (iii) the full-length complement of (i) or (ii) (Sambrook et al., 1989, Molecular Cloning, A Laboratory Manual, 2d edition, Cold Spring Harbor, New York). In an embodiment, the polypeptide has been isolated.

In another embodiment, the present invention relates to an polypeptide having DNase activity encoded by a polynucleotide having a sequence identity to the mature polypeptide coding sequence of SEQ ID NO: 1 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to an polypeptide having DNase activity encoded by a polynucleotide having a sequence identity to the mature polypeptide coding sequence of SEQ ID NO: 6, SEQ ID NO: 7 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% and wherein the polypeptide is used for preventing, reducing or removing static electricity from an item.

In another embodiment, the present invention relates to variants of the mature polypeptide of SEQ ID NO: 2 comprising a substitution, deletion, and/or insertion at one or more (e.g., several) positions. In an embodiment, the number of amino acid substitutions, deletions and/or insertions introduced into the mature polypeptide of SEQ ID NO: 2 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a polyhistidine tract, an antigenic epitope or a binding domain.

In another embodiment, the present invention relates to variants of the mature polypeptide of SEQ ID NO: 3 comprising a substitution, deletion, and/or insertion at one or more (e.g., several) positions. In an embodiment, the number of amino acid substitutions, deletions and/or insertions introduced into the mature polypeptide of SEQ ID NO: 3 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a polyhistidine tract, an antigenic epitope or a binding domain.

The polypeptide having DNase activity can also be obtained from *Trichoderma*, for example from *Trichoderma harzianum*. In an embodiment, the present invention relates to polypeptides having a sequence identity to the mature polypeptide of SEQ ID NO: 5 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have DNase activity. In one aspect, the polypeptides differ by up to 10 amino acids, e.g., 1, 2, 3, 4, 5, 6, 7, 8, 9, or 10, from the mature polypeptide of SEQ ID NO: 5.

In an embodiment, the polypeptide has been isolated. A polypeptide of the present invention preferably comprises or consists of the amino acid sequence of SEQ ID NO: 5 or an allelic variant thereof; or is a fragment thereof having DNase activity. In another aspect, the polypeptide comprises or consists of the mature polypeptide of SEQ ID NO: 5. In another aspect, the polypeptide comprises or consists of amino acids 1 to 188 of SEQ ID NO: 5.

In another embodiment, the present invention relates to an isolated polypeptide having DNase activity encoded by a polynucleotide that hybridizes under low stringency conditions with (i) the mature polypeptide coding sequence of SEQ ID NO: 4, (ii) the cDNA sequence thereof, or (iii) the full-length complement of (i) or (ii) (Sambrook et al., 1989, Molecular Cloning, A Laboratory Manual, 2d edition, Cold Spring Harbor, New York). In an embodiment, the polypeptide has been isolated.

The polynucleotide of SEQ ID NO: 1 or SEQ ID NO: 4 or a subsequence thereof, as well as the polypeptide of SEQ ID NO: 5, SEQ ID NO: 2, SEQ ID NO: 3 or a fragment thereof, may be used to design nucleic acid probes to identify and clone DNA encoding polypeptides having DNase activity from strains of different genera or species according to methods well known in the art.

In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having DNase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 4 or a subsequence thereof, the carrier material is used in a Southern blot.

For purposes of the present invention, hybridization indicates that the polynucleotide hybridizes to a labeled nucleic acid probe corresponding to (i) SEQ ID NO: 1 or SEQ ID NO: 4; (ii) the mature polypeptide coding sequence of SEQ ID NO: 1 or SEQ ID NO: 4; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In another embodiment, the present invention relates to an polypeptide having DNase activity encoded by a polynucleotide having a sequence identity to the mature polypeptide coding sequence of SEQ ID NO: 1 or SEQ ID NO: 4 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 2, SEQ ID NO: 3 or SEQ ID NO: 5 comprising a substitution, deletion, and/or insertion at one or more (e.g., several) positions. In an embodiment, the number of amino acid substitutions, deletions and/or insertions introduced into the mature polypeptide of SEQ ID NO: 2, SEQ ID NO: 3 or SEQ ID NO: 5 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

The polypeptide having DNase activity can also be obtained from Bacillus, for example from Bacillus substilis or Bacillus licheniformis.

In an embodiment, the present invention relates to polypeptides having a sequence identity to the mature polypeptide of SEQ ID NO: 6 or SEQ ID NO: 7 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have DNase activity. In one aspect, the polypeptides differ by up to 10 amino acids, e.g., 1, 2, 3, 4, 5, 6, 7, 8, 9, or 10, from the mature polypeptide of SEQ ID NO: 6 or SEQ ID NO: 7.

In an embodiment, the polypeptide has been isolated. A polypeptide of the present invention preferably comprises or consists of the amino acid sequence of SEQ ID NO: 6, SEQ ID NO: 7 or an allelic variant thereof; or is a fragment thereof having DNase activity. In another aspect, the polypeptide comprises or consists of the mature polypeptide of SEQ ID NO: 6 or SEQ ID NO: 7. In another aspect, the polypeptide comprises or consists of amino acids 1 to 110 of SEQ ID NO: 6 or amino acids 1 to 109 of SEQ ID NO: 7.

In another embodiment, the present invention relates to an polypeptide having DNase activity encoded by a polynucleotide having a sequence identity to the mature polypeptide coding sequence of SEQ ID NO: 6, SEQ ID NO: 7 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 6 or SEQ ID NO: 7 comprising a substitution, deletion, and/or insertion at one or more (e.g., several) positions. In an embodiment, the number of amino acid substitutions, deletions and/or insertions introduced into the mature polypeptide of SEQ ID NO: 6 or SEQ ID NO: 7 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for DNase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30:10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Deoxyribonuclease (DNase)

A polypeptide having DNase activity or a deoxyribonuclease (DNase) is any enzyme that catalyzes the hydrolytic cleavage of phosphodiester linkages in the DNA backbone, thus degrading DNA. The two terms polypeptide having DNase activity and DNase are used interchangeably.

According to the present invention, a DNase which is obtainable from a fungus is preferred; in particular a DNase which is obtainable from a *Aspergillus* is preferred; in particular a DNase which is obtainable from *Aspergillus oryzae* is preferred. In one embodiment of the present invention, the polypeptide having deoxyribonuclease activity is not the S1 nuclease from *Aspergillus oryzae*.

The DNase used in the present invention includes the mature polypeptide of SEQ ID NO: 2, shown as amino acids 1 to 206 of SEQ ID NO: 2, which is obtained from *Aspergillus oryzae*. The polypeptide having DNase activity can be obtained from *Aspergillus*, for example from *Aspergillus oryzae*. In one embodiment of the invention the polypeptide having DNase activity is the claimed polypeptide.

One aspect of the present invention relates to isolated polypeptides having a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have DNase activity. In one aspect, the polypeptides differ by up to 10 amino acids, e.g., 1, 2, 3, 4, 5, 6, 7, 8, 9, or 10, from the mature polypeptide of SEQ ID NO: 2.

In an embodiment, the present invention relates to isolated polypeptides having a sequence identity to the mature polypeptide of SEQ ID NO: 3 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have DNase activity. In one aspect, the polypeptides differ by up to 10 amino acids, e.g., 1, 2, 3, 4, 5, 6, 7, 8, 9, or 10, from the mature polypeptide of SEQ ID NO: 3.

In an embodiment, the present invention relates to isolated polypeptides having a sequence identity to SEQ ID NO: 8 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have DNase activity. In one aspect, the polypeptides differ by up to 10 amino acids, e.g., 1, 2, 3, 4, 5, 6, 7, 8, 9, or 10, from the mature polypeptide of SEQ ID NO: 8.

A polypeptide of the present invention preferably comprises or consists of the amino acid sequence of SEQ ID NO: 2 or an allelic variant thereof; or is a fragment thereof having DNase activity. In another aspect, the polypeptide comprises or consists of the mature polypeptide of SEQ ID NO: 2. In another aspect, the polypeptide comprises or consists of amino acids 1 to 206 of SEQ ID NO: 2.

In an embodiment, the polypeptide has been isolated. A polypeptide of the present invention preferably comprises or consists of the amino acid sequence of SEQ ID NO: 3 or an allelic variant thereof; or is a fragment thereof having DNase activity. In another aspect, the polypeptide comprises or consists of the mature polypeptide of SEQ ID NO: 3. In another aspect, the polypeptide comprises or consists of amino acids 1 to 204 of SEQ ID NO: 3. One aspect of the present invention relates to a composition comprising or consisting of a polypeptide consisting of the amino acid sequence of SEQ ID NO: 8 and a polypeptide of the present invention consisting of the amino acid sequence of SEQ ID NO: 3.

In another embodiment, the present invention relates to an isolated polypeptide having DNase activity encoded by a polynucleotide that hybridizes under low stringency conditions with (i) the mature polypeptide coding sequence of SEQ ID NO: 1, (ii) the cDNA sequence thereof, or (iii) the full-length complement of (i) or (ii) (Sambrook et al., 1989, Molecular Cloning, A Laboratory Manual, 2d edition, Cold Spring Harbor, New York). In an embodiment, the polypeptide has been isolated.

In another embodiment, the present invention relates to an isolated polypeptide having DNase activity encoded by a polynucleotide that hybridizes under low-medium stringency conditions with (i) the mature polypeptide coding sequence of SEQ ID NO: 1, (ii) the cDNA sequence thereof, or (iii) the full-length complement of (i) or (ii). In an embodiment, the polypeptide has been isolated.

In another embodiment, the present invention relates to an isolated polypeptide having DNase activity encoded by a polynucleotide that hybridizes under medium stringency conditions with (i) the mature polypeptide coding sequence of SEQ ID NO: 1, (ii) the cDNA sequence thereof, or (iii) the full-length complement of (i) or (ii). In an embodiment, the polypeptide has been isolated.

In another embodiment, the present invention relates to an isolated polypeptide having DNase activity encoded by a polynucleotide that hybridizes under medium-high stringency conditions with (i) the mature polypeptide coding sequence of SEQ ID NO: 1, (ii) the cDNA sequence thereof, or (iii) the full-length complement of (i) or (ii). In an embodiment, the polypeptide has been isolated.

In another embodiment, the present invention relates to an isolated polypeptide having DNase activity encoded by a polynucleotide that hybridizes under high stringency conditions with (i) the mature polypeptide coding sequence of SEQ ID NO: 1, (ii) the cDNA sequence thereof, or (iii) the full-length complement of (i) or (ii). In an embodiment, the polypeptide has been isolated.

In another embodiment, the present invention relates to an isolated polypeptide having DNase activity encoded by a polynucleotide that hybridizes under very high stringency conditions with (i) the mature polypeptide coding sequence of SEQ ID NO: 1, (ii) the cDNA sequence thereof, or (iii) the full-length complement of (i) or (ii). In an embodiment, the polypeptide has been isolated.

In another embodiment, the present invention relates to an polypeptide having DNase activity encoded by a polynucleotide having a sequence identity to the mature polypeptide coding sequence of SEQ ID NO: 1 or the cDNA sequence thereof of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 2 comprising a substitution, deletion, and/or insertion at one or more (e.g., several) positions. In an embodiment, the number of amino acid substitutions, deletions and/or insertions introduced into the mature polypeptide of SEQ ID NO: 2 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

In another embodiment, the present invention relates to variants of the mature polypeptide of SEQ ID NO: 3 comprising a substitution, deletion, and/or insertion at one or more (e.g., several) positions. In an embodiment, the number of amino acid substitutions, deletions and/or insertions introduced into the mature polypeptide of SEQ ID NO: 3 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

The DNase enzyme may comprise or consist of the amino acid sequence shown as amino acids −37 to 206 of SEQ ID NO: 2 or a fragment thereof that has DNase activity, such as the mature polypeptide. Or the DNase enzyme may comprise or consist of a fragment of amino acids −37 to 206 of SEQ ID NO: 2 or amino acids 1 to 206 of SEQ ID NO: 2 for which fragment one or more amino acids is deleted from the amino and/or carboxyl terminus of SEQ ID NO: 2.

The DNase enzyme may comprise or consist of the amino acid sequence shown as amino acids 1 to 206 of SEQ ID NO: 3 or a fragment thereof that has DNase activity, such as the mature polypeptide. Or the DNase enzyme may comprise or consist of a fragment of amino acids 1 to 206 of SEQ ID NO: 3 or amino acids 1 to 206 of SEQ ID NO: 3 for which fragment one or more amino acids is deleted from the amino and/or carboxyl terminus of SEQ ID NO: 3.

The DNase enzyme may comprise or consist of the amino acid sequence shown as amino acids 1 to 206 of SEQ ID NO: 8 or a fragment thereof that has DNase activity, such as the mature polypeptide. Or the DNase enzyme may comprise or consist of a fragment of amino acids 1 to 206 of SEQ ID NO: 8 or amino acids 1 to 206 of SEQ ID NO: 8 for which fragment one or more amino acids is deleted from the amino and/or carboxyl terminus of SEQ ID NO: 8.

The present invention also provides DNase polypeptides that are substantially homologous to the polypeptides above, and species homologs (paralogs or orthologs) thereof. The term "substantially homologous" is used herein to denote polypeptides being at least 80%, preferably at least 85%, more preferably at least 90%, more preferably at least 95%, even more preferably at least 97% identical, and most preferably at least 99% or more identical to the amino acid sequence of SEQ ID NO: 2 or to the amino acid sequence of SEQ ID NO: 3, or a fragment thereof that has DNase activity, or its orthologs or paralogs.

In another embodiment, the DNase of SEQ ID NO: 2 comprises a substitution, deletion, and/or insertion at one or more (e.g., several) positions. In another embodiment, the DNase of SEQ ID NO: 3 comprises a substitution, deletion, and/or insertion at one or more (e.g., several) positions. In an embodiment, the number of amino acid substitutions, deletions and/or insertions introduced into the mature polypeptide of SEQ ID NO: 2 or into the mature polypeptide of SEQ ID NO: 3 is not more than 10, e.g., 1, 2, 3, 4, 5, 6, 7, 8 or 9. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

According to the present invention, a DNase which is obtainable from a fungus is preferred; in particular a DNase which is obtainable from a *Trichoderma* is preferred; in particular a DNase which is obtainable from *Trichoderma harzianum* is preferred.

The DNase used in the present invention includes the mature polypeptide of SEQ ID NO: 5, shown as amino acids 1 to 188 of SEQ ID NO: 5, which is obtained from *Trichoderma harzianum*.

The DNase enzyme may comprise or consist of the amino acid sequence shown as amino acids –17 to 188 of SEQ ID NO: 5 or a fragment thereof that has DNase activity, such as the mature polypeptide. Or the DNase enzyme may comprise or consist of a fragment of amino acids –17 to 188 of SEQ ID NO: 5 or amino acids 1 to 188 of SEQ ID NO: 5 for which fragment one or more amino acids is deleted from the amino and/or carboxyl terminus of SEQ ID NO: 5.

The present invention also provides DNase polypeptides that are substantially homologous to the polypeptides above, and species homologs (paralogs or orthologs) thereof. The term "substantially homologous" is used herein to denote polypeptides being at least 80%, preferably at least 85%, more preferably at least 90%, more preferably at least 95%, even more preferably at least 97% identical, and most preferably at least 99% or more identical to the amino acid sequence of SEQ ID NO: 5, or a fragment thereof that has DNase activity, or its orthologs or paralogs.

According to the present invention, a DNase which is obtainable from a bacterium is preferred; in particular a DNase which is obtainable from a *Bacillus* is preferred; in particular a DNase which is obtainable from *Bacillus subtilis* or *Bacillus licheniformis* is preferred.

The DNase used in the present invention includes the mature polypeptide of SEQ ID NO: 6, shown as amino acids 1 to 110 of SEQ ID NO: 6, which is derived from *Bacillus subtilis*; or the mature polypeptide of SEQ ID NO: 7, shown as amino acids 1 to 109 of SEQ ID NO: 7, which is derived from *Bacillus licheniformis*.

The DNase enzyme may comprise or consist of the amino acid sequence shown as amino acids –26 to 110 of SEQ ID NO: 6 or amino acids –33 to 109 of SEQ ID NO: 7, or a fragment thereof that has DNase activity, such as the mature polypeptide. A fragment of amino acids –26 to 110 of SEQ ID NO: 6, or amino acids 1 to 110 of SEQ ID NO: 6 is a polypeptide, which has one or more amino acids deleted from the amino and/or carboxyl terminus of SEQ ID NO: 6. A fragment of or amino acids –33 to 109 of SEQ ID NO: 7, or 1 to 109 of SEQ ID NO: 7 is a polypeptide, which has one or more amino acids deleted from the amino and/or carboxyl terminus of SEQ ID NO: 7.

The present invention also provides DNase polypeptides that are substantially homologous to the polypeptides above, and species homologs (paralogs or orthologs) thereof. The term "substantially homologous" is used herein to denote polypeptides being at least 80%, preferably at least 85%, more preferably at least 90%, more preferably at least 95%, even more preferably at least 97% identical, and most preferably at least 99% or more identical to the amino acid sequence of SEQ ID NO: 6 or SEQ ID NO: 7, or a fragment thereof that has DNase activity, or its orthologs or paralogs.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for DNase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wiodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The concentration of the DNase in the wash liquor is typically in the range of 0.00004-100 ppm enzyme protein, such as in the range of 0.00008-100, in the range of 0.0001-100, in the range of 0.0002-100, in the range of 0.0004-100, in the range of 0.0008-100, in the range of 0.001-100 ppm enzyme protein, 0.01-100 ppm enzyme protein, preferably 0.05-50 ppm enzyme protein, more preferably 0.1-50 ppm enzyme protein, more preferably 0.1-30 ppm enzyme protein, more preferably 0.5-20 ppm enzyme protein, and most preferably 0.5-10 ppm enzyme protein.

The DNase of the present invention may be added to a detergent composition in an amount corresponding to at least 0.002 mg of DNase protein, such as at least 0.004 mg of DNase protein, at least 0.006 mg of DNase protein, at least 0.008 mg of DNase protein, at least 0.01 mg of DNase protein, at least 0.1 mg of protein, preferably at least 1 mg of protein, more preferably at least 10 mg of protein, even more preferably at least 15 mg of protein, most preferably at least 20 mg of protein, and even most preferably at least 25 mg of protein. Thus, the detergent composition may comprise at least 0.00008% DNase protein, preferably at least 0.002%, 0.003%, 0.004%, 0.005%, 0.006%, 0.008%, 0.01%, 0.02%, 0.03%, 0.05%, 0.1%, 0.2%, 0.3%, 0.4%, 0.6%, 0.7%, 0.8%, 0.9% or 1.0% of DNase protein.

The DNase of the detergent composition of the invention may be stabilized using conventional stabilizing agents, e.g. a polyol such as propylene glycol or glycerol, a sugar or sugar alcohol, lactic acid, boric acid, or a boric acid derivative, e.g. an aromatic borate ester, or a phenyl boronic acid derivative such as 4-formylphenyl boronic acid, and the composition may be formulated as described in, for example, WO92/19709 and WO92/19708.

A polypeptide of the present invention may also be incorporated in the detergent formulations disclosed in WO97/07202, which is hereby incorporated by reference.

Detergent Compositions

In one embodiment, the invention is directed to detergent compositions comprising an enzyme of the present invention in combination with one or more additional cleaning composition components. The choice of additional components is within the skill of the artisan and includes conventional ingredients, including the exemplary non-limiting components set forth below.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and may include any conventional surfactant(s) known in the art.

When included therein the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

When included therein the detergent will usually contain from about 0% to about 40% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0% to about 40% by weight of a zwitterionic surfactant. Non-limiting examples of zwitterionic surfactants include betaines such as alkyldimethylbetaines, sulfobetaines, and combinations thereof.

Hydrotropes A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 50% of a detergent builder or co-builder, or a mixture thereof. The builder and/or co-builder may particularly be a chelating agent that forms water-soluble complexes with Ca and Mg. Any builder and/or co-builder known in the art for use in detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis(methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Bleaching Systems

The detergent may contain 0-30% by weight, such as about 1% to about 20%, of a bleaching system. Any bleaching system known in the art for use in detergents may be utilized. Suitable bleaching system components include bleaching catalysts, photobleaches, bleach activators, sources of hydrogen peroxide such as sodium percarbonate, sodium perborates and hydrogen peroxide-urea (1:1), preformed peracids and mixtures thereof. Suitable preformed peracids include, but are not limited to, peroxycarboxylic acids and salts, diperoxydicarboxylic acids, perimidic acids and salts, peroxymonosulfuric acids and salts, for example, Oxone®, and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable examples are tetraacetylethylenediamine (TAED), sodium 4-[(3,5,5-trimethylhexanoyl)oxy]benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that it is environmentally friendly. Furthermore acetyl triethyl citrate and triacetin have good hydrolytical stability in the product upon storage and are efficient bleach activators. Finally ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

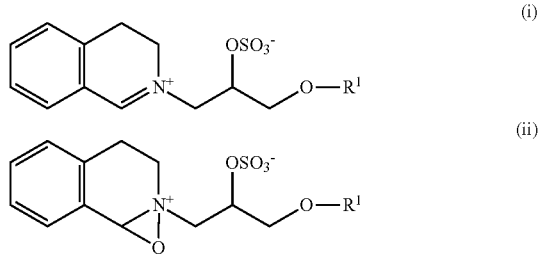

(iii) and mixtures thereof;
wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl. Other exemplary bleaching systems are described, e.g. in WO2007/087258, WO2007/087244, WO2007/087259, EP1867708 (Vitamin K) and WO2007/087242. Suitable photobleaches may for example be sulfonated zinc or aluminium phthalocyanines.

Preferably the bleach component comprises a source of peracid in addition to bleach catalyst, particularly organic bleach catalyst. The source of peracid may be selected from (a) preformed peracid; (b) percarbonate, perborate or persulfate salt (hydrogen peroxide source) preferably in combination with a bleach activator; and (c) perhydrolase enzyme and an ester for forming peracid in situ in the presence of water in a textile treatment step.

Polymers

The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquatemium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Enzymes

The detergent additive as well as the detergent composition may comprise one or more additional enzymes such as a protease, lipase, cutinase, an amylase, carbohydrase, cellulase, pectinase, mannanase, arabinase, galactanase, xylanase, oxidase, e.g., alaccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and WO99/001544.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Proteases:

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those obtained from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin *lentus*, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases obtained from *Cellumonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those obtained from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V4I, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases:

Suitable lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus*

*stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases:

Suitable amylases which can be used together with the DNase may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase obtained from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase obtained from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™ Stainzyme Pus™, Natalase™, Liquozyme X and BAN™ (from Novozymes A/S), and Rapidase™, Purastar™/Effectenz™, Powerase and Preferenz S100 (from Genencor International Inc./DuPont).

Peroxidases/Oxidases:

A peroxidase according to the invention is a peroxidase enzyme comprised by the enzyme classification EC 1.11.1.7, as set out by the Nomenclature Committee of the International Union of Biochemistry and Molecular Biology (IUBMB), or any fragment obtained therefrom, exhibiting peroxidase activity.

Suitable peroxidases include those of plant, bacterial or fungal origin. Chemically modified or protein engineered mutants are included. Examples of useful peroxidases include peroxidases from Coprinopsis, e.g., from C. cinerea (EP 179,486), and variants thereof as those described in WO 93/24618, WO 95/10602, and WO 98/15257.

A peroxidase according to the invention also includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as Caldariomyces, e.g., C. fumago, Alternaria, Curvularia, e.g., C. verruculosa and C. inaequalis, Drechslera, Ulocladium and Botrytis.

Haloperoxidases have also been isolated from bacteria such as Pseudomonas, e.g., P. pyrrocinia and Streptomyces, e.g., S. aureofaciens.

In a preferred embodiment, the haloperoxidase is derivable from Curvularia sp., in particular Curvularia verruculosa or Curvularia inaequalis, such as C. inaequalis CBS 102.42 as described in WO 95/27046; or C. verruculosa CBS 147.63 or C. verruculosa CBS 444.70 as described in WO 97/04102; or from Drechslera hartlebii as described in WO 01/79459, Dendryphiella salina as described in WO 01/79458, Phaeotrichoconis crotalarie as described in WO 01/79461, or Geniculosporium sp. as described in WO 01/79460.

An oxidase according to the invention include, in particular, any laccase enzyme comprised by the enzyme classification EC 1.10.3.2, or any fragment obtained therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be obtained from plants, bacteria or fungi (including filamentous fungi and yeasts).

Suitable examples from fungi include a laccase derivable from a strain of Aspergillus, Neurospora, e.g., N. crassa, Podospora, Botfytis, Collybia, Fomes, Lentinus, Pleurotus, Trametes, e.g., T. villosa and T. versicolor, Rhizoctonia, e.g., R. solani, Coprinopsis, e.g., C. cinerea, C. comatus, C. friesii, and C. plicatilis, Psathyrella, e.g., P. condelleana, Panaeolus, e.g., P. papilionaceus, Myceliophthora, e.g., M. thermophila, Schytalidium, e.g., S. thermophilum, Polyporus, e.g., P. pinsitus, Phlebia, e.g., P. radiata (WO 92/01046), or Coriolus, e.g., C. hirsutus (JP 2238885).

Suitable examples from bacteria include a laccase derivable from a strain of Bacillus.

A laccase obtained from Coprinopsis or Myceliophthora is preferred; in particular a laccase obtained from Coprinopsis cinerea, as disclosed in WO 97/08325; or from Myceliophthora thermophila, as disclosed in WO 95/33836.

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Other Materials

Any detergent components known in the art for use in detergents may also be utilized. Other optional detergent components include anti-corrosion agents, anti-shrink agents, anti-soil redeposition agents, anti-wrinkling agents, bactericides, fungicides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in detergents may be utilized. The choice of such ingredients is well within the skill of the artisan.

Dispersants

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2, 2'-disulfonate, 4,4'-bis-(4-phenyl-1,2,3-triazol-2-yl)stilbene-2,2'-disulfonate and sodium 5-(2H-naphtho[1,2-d][1,2,3] triazol-2-yl)-2-[(E)-2-phenylvinyl]benzenesulfonate.

Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Anti-Static Agents

An antistatic agent is a compound used for treatment of materials or their surfaces in order to reduce or eliminate buildup of static electricity. The antistatic agent is different from DNase.

Common antistatic agents are based on long-chain aliphatic amines (optionally ethoxylated) and amides, quaternary ammonium salts (e.g., behentrimonium chloride or cocamidopropyl betaine), esters of phosphoric acid, polyethylene glycol esters, or polyols. Indium tin oxide can be used as transparent antistatic coating of windows. It is also possible to use conductive polymers, like PEDOT:PSS and conducting polymer nanofibers, particularly polyaniline nanofibers. In general these systems are not very durable for coating, especially antimony tin oxide is used for durable systems, often in its nano form, its is then formulated to a final coating.

Antistatic agents are also added to some military jet fuels, to impart electrical conductivity to them and avoid buildup of static charge that could lead to sparks igniting fuel vapors. Stadis 450 is the agent added to some distillate fuels, commercial jet fuels, and to the military JP-8. Stadis 425 is a similar compound, for use in distillate fuels. Statsafe products are used in non-fuel applications.

One group of antistatic compounds are the methanesulfonamide antistatic agents substituted on the nitrogen atom and having the formula:

$$RNHSO_2CH_3.$$

wherein R is a secondary aliphatic hydrocarbon chain containing at least 8 carbons.

The methanesulfonamides substituted on the nitrogen atom with one secondary long aliphatic chain containing 8-22 carbons reduces or prevents the generation of static electricity on cotton and synthetic fabrics during laundering. These antistatic properties can be imparted to fabrics by laundering in a detergent composition containing said methanesulfonamides which are completely compatible with anionic, non-ionic, cationic and amphoteric detergents. This same treatment has been found to additionally confer a soft hand on cotton fabrics. These beneficial effects are achieved without yellowing or discoloration of the fabrics and without interference with the action of optical brighteners that may be present in the detergent composition. The methanesulfonamides of instant invention can be prepared as described in U.S. Pat. No. 4,260,497.

Another group of antistatic compounds are cationic quaternary ammonium compounds as described in WO2008/000333, WO95/29218, WO2011/011247 or WO2009/158388.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid or the composition is comprised on a sheet or wipe.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent.

A liquid or gel detergent may be non-aqueous.

Laundry Soap Bars

The DNase of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g. a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing a soap, DNase, optionally one or more additional enzymes, a protease inhibitor, and a salt of a monovalent cation and an organic anion may be prepared and and the mixture is then plodded. The DNase and optional additional enzymes may be added at the same time as the protease inhibitor for example in liquid form.

Besides the mixing step and the plodding step, the process may further comprise the steps of milling, extruding, cutting, stamping, cooling and/or wrapping.

Formulation of Enzyme in Co-Granule

The DNase may be formulated as a granule for example as a co-granule that combines one or more enzymes. Each enzyme will then be present in more granules securing a more uniform distribution of enzymes in the detergent. This also reduces the physical segregation of different enzymes due to different particle sizes. Methods for producing multi-enzyme co-granulates for the detergent industry are disclosed in the IP.com disclosure IPCOM000200739D.

Another example of formulation of enzymes by the use of co-granulates are disclosed in WO 2013/188331, which relates to a detergent composition comprising (a) a multi-enzyme co-granule; (b) less than 10 wt zeolite (anhydrous basis); and (c) less than 10 wt phosphate salt (anhydrous basis), wherein said enzyme co-granule comprises from 10 to 98 wt % moisture sink component and the composition additionally comprises from 20 to 80 wt % detergent moisture sink component. WO 2013/188331 also relates to a method of treating and/or cleaning a surface, preferably a fabric surface comprising the steps of (i) contacting said surface with the detergent composition as claimed and described herein in an aqueous wash liquor, (ii) rinsing and/or drying the surface.

The multi-enzyme co-granule may comprise a DNase and (a) one or more enzymes selected from the group consisting of first-wash lipases, cleaning cellulases, xyloglucanases, perhydrolases, peroxidases, lipoxygenases, laccases and mixtures thereof; and (b) one or more enzymes selected from the group consisting of hemicellulases, proteases, care cellulases, cellobiose dehydrogenases, xylanases, phospholipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof.

The Invention is Further Summarized in the Following Paragraphs:

1. Use of a polypeptide having DNase activity for preventing, reducing or removing static electricity on and/or from an item on which static electricity may accumulate.
2. Use according to paragraph 1, wherein the item is a textile or a hard surface.
3. Use according to any of paragraphs 1-2, wherein the polypeptide having DNase activity is sprayed onto the item.
4. Use according to any of paragraphs 1-2, wherein the item is contacted with a liquid solution comprising a polypeptide having DNase activity.
5. Use according to any of paragraphs 1-4, wherein the liquid solution is a wash liquor.
6. Use according to any of paragraphs 1-2 and 4-5, wherein the item is impregnated with the polypeptide having DNase activity.
7. Use according to any of the preceding paragraphs, wherein the item is coated with the polypeptide having DNase activity.
8. Use according to any of paragraphs 1-3, wherein the item is painted with the polypeptide having DNase activity.
9. Use according to any of the preceding paragraphs, wherein the polypeptide having DNase activity is of animal, vegetable or microbial origin.
10. Use according to paragraph 9, wherein the polypeptide is of human origin.
11. Use according to paragraph 9, wherein the polypeptide is obtained from mung bean.
12. Use according to paragraph 9, wherein the polypeptide is of bacterial or fungal origin.
13. Use according to paragraph 12, wherein the polypeptide is of fungal origin and the polypeptide is selected from the group consisting of:
    a. a polypeptide having at least 60% sequence identity to the mature polypeptide of SEQ ID NO: 2, a polypeptide having at least 60% sequence identity to the mature polypeptide of SEQ ID NO: 3, a polypeptide having at least 60% sequence identity to the mature polypeptide of SEQ ID NO: 5 or a polypeptide having at least 60% sequence identity to the mature polypeptide of SEQ ID NO: 8
    b. a polypeptide encoded by a polynucleotide that hybridizes under low stringency conditions with
        i. the mature polypeptide coding sequence of SEQ ID NO: 1 or the mature polypeptide coding sequence of SEQ ID NO: 4
        ii. the cDNA sequence thereof, or
        iii. the full-length complement of (i) or (ii);
    c. a polypeptide encoded by a polynucleotide having at least 60% sequence identity to the mature polypeptide coding sequence of SEQ ID NO: 1 or the cDNA sequence thereof or a polypeptide encoded by a polynucleotide having at least 60% sequence identity to the mature polypeptide coding sequence of SEQ ID NO: 4 or the cDNA sequence thereof;
    d. a variant of the mature polypeptide of SEQ ID NO: 2 comprising a substitution, deletion, and/or insertion at one or more positions, a variant of the mature polypeptide of SEQ ID NO: 3 comprising a substitution, deletion, and/or insertion at one or more positions, a variant of the mature polypeptide of SEQ ID NO: 5 comprising a substitution, deletion, and/or insertion at one or more positions or a variant of the mature polypeptide of SEQ ID NO: 8 comprising a substitution, deletion, and/or insertion at one or more positions; and
    e. a fragment of the polypeptide of (a), (b), (c), or (d) that has DNase activity;
14. Use according to paragraph 12, wherein the polypeptide is of bacterial origin and the polypeptide is selected from the group consisting of:
    a. a polypeptide having at least 60% sequence identity to the mature polypeptide of SEQ ID NO: 6 or a polypeptide having at least 60% sequence identity to the mature polypeptide of SEQ ID NO: 7;
    b. a variant of the mature polypeptide of SEQ ID NO: 6 comprising a substitution, deletion, and/or insertion at one or more positions or a variant of the mature polypeptide of SEQ ID NO: 7 comprising a substitution, deletion, and/or insertion at one or more positions; and
    c. a fragment of the polypeptide of (a) or (b) that has DNase activity;
15. Use according to any of paragraphs 13-14, wherein the polypeptide is having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, to the mature polypeptide of SEQ ID NO: 3, to the mature polypeptide of SEQ ID NO: 5, to the mature polypeptide of SEQ ID NO: 6, to the mature polypeptide of SEQ ID NO: 7 or, to the mature polypeptide of SEQ ID NO: 8.

16. Use according to any of paragraphs 13-15, wherein the polypeptide comprises or consists of SEQ ID NO: 2 or the mature polypeptide of SEQ ID NO: 2, the polypeptide comprises or consists of SEQ ID NO: 3 or the mature polypeptide of SEQ ID NO: 3, the polypeptide comprises or consists of SEQ ID NO: 5 or the mature polypeptide of SEQ ID NO: 5, the polypeptide comprises or consists of SEQ ID NO: 6 or the mature polypeptide of SEQ ID NO: 6, the polypeptide comprises or consists of SEQ ID NO: 7 or the mature polypeptide of SEQ ID NO: 7 or the polypeptide comprises or consists of SEQ ID NO: 8 or the mature polypeptide of SEQ ID NO: 8.

17. Use according to any of paragraphs 13-16, wherein the mature polypeptide is amino acids 1 to 206 of SEQ ID NO: 2, amino acids 1 to 206 of SEQ ID NO: 3, amino acids 1 to 188 of SEQ ID NO: 5, amino acids 1 to 110 of SEQ ID NO: 6 or amino acids 1 to 109 of SEQ ID NO: 7 or amino acids 1 to 206 of SEQ ID NO: 8.

18. Use according to any of paragraphs 13-17, wherein the polypeptide is a variant of the mature polypeptide of SEQ ID NO: 2, SEQ ID NO: 3, SEQ ID NO: 5, SEQ ID NO: 6, SEQ ID NO: 7 or SEQ ID NO: 8, wherein the variant comprises a substitution, deletion, and/or insertion at one or more positions or a variant of the mature polypeptide of SEQ ID NO: 2, SEQ ID NO: 3, SEQ ID NO: 5, SEQ ID NO: 6, SEQ ID NO: 7 or SEQ ID NO: 8 which comprises a substitution, deletion, and/or insertion at one or more positions.

19. Use according to any of paragraphs 13-17, wherein the polypeptide is a fragment of SEQ ID NO: 2, SEQ ID NO: 3, SEQ ID NO: 5, SEQ ID NO: 6, SEQ ID NO: 7 or SEQ ID NO: 8, wherein the fragment has DNase activity.

20. A composition for preventing, reducing or removing static electricity, wherein the composition comprises a polypeptide having deoxyribonuclease (DNase) activity.

21. Composition according paragraph 20, wherein the composition is a laundry detergent composition; a dish wash detergent composition; a composition for hard surface cleaning; a laundry softening composition; or a composition for personal care.

22. Composition according to any of paragraphs 20-21, wherein the composition is laundry detergent composition; a dish wash detergent composition; or a composition for hard surface cleaning.

23. Composition according to any of paragraphs 20-21, wherein the composition is a laundry softening composition.

24. Composition according to paragraph 23, wherein the laundry softening composition is incorporated into a sheet or a wipe.

25. Composition according to any of the preceding composition paragraph, wherein the composition further comprises an antistatic agent different from a polypeptide having DNase activity.

26. Composition according to any of the preceding composition paragraphs, wherein the composition further comprises surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, bacteriocides, fungicides and/or pigments.

27. Composition according to any of the preceding composition paragraphs, wherein the composition further comprises one or more enzymes selected from the group consisting of proteases, lipases, cutinases, amylases, carbohydrases, cellulases, pectinases, mannanases, arabinases, galactanases, xylanases and oxidases.

28. Composition according to any of the preceding composition paragraphs, wherein the polypeptide having DNase activity is of animal, vegetable or microbial origin.

29. Composition according to any of the preceding composition paragraphs, wherein the polypeptide is of human origin.

30. Composition according to any of the preceding composition paragraphs, wherein the polypeptide is obtained from mung bean.

31. Composition according to any of the preceding composition paragraphs, wherein the polypeptide is of bacterial or fungal origin.

32. Composition according to paragraph 31, wherein the polypeptide is of fungal origin and the polypeptide is selected from the group consisting of:
    a. a polypeptide having at least 60% sequence identity to the mature polypeptide of SEQ ID NO: 2, a polypeptide having at least 60% sequence identity to the mature polypeptide of SEQ ID NO: 3, a polypeptide having at least 60% sequence identity to the mature polypeptide of SEQ ID NO: 5 or a polypeptide having at least 60% sequence identity to the mature polypeptide of SEQ ID NO: 8;
    b. a polypeptide encoded by a polynucleotide that hybridizes under low stringency conditions with
        i. the mature polypeptide coding sequence of SEQ ID NO: 1 or the mature polypeptide coding sequence of SEQ ID NO: 4
        ii. the cDNA sequence thereof, or
        iii. the full-length complement of (i) or (ii);
    c. a polypeptide encoded by a polynucleotide having at least 60% sequence identity to the mature polypeptide coding sequence of SEQ ID NO: 1 or the cDNA sequence thereof or a polypeptide encoded by a polynucleotide having at least 60% sequence identity to the mature polypeptide coding sequence of SEQ ID NO: 4 or the cDNA sequence thereof;
    d. a variant of the mature polypeptide of SEQ ID NO: 2 comprising a substitution, deletion, and/or insertion at one or more positions, a variant of the mature polypeptide of SEQ ID NO: 3 comprising a substitution, deletion, and/or insertion at one or more positions, a variant of the mature polypeptide of SEQ ID NO: 5 comprising a substitution, deletion, and/or insertion at one or more positions or a variant of the mature polypeptide of SEQ ID NO: 8 comprising a substitution, deletion, and/or insertion at one or more positions; and
    e. a fragment of the polypeptide of (a), (b), (c), or (d) that has DNase activity;

33. Composition according to paragraph 31, wherein the polypeptide is of bacterial origin and the polypeptide is selected from the group consisting of:
    a. a polypeptide having at least 60% sequence identity to the mature polypeptide of SEQ ID NO: 6 or a polypeptide having at least 60% sequence identity to the mature polypeptide of SEQ ID NO: 7;

b. a variant of the mature polypeptide of SEQ ID NO: 6 comprising a substitution, deletion, and/or insertion at one or more positions or a variant of the mature polypeptide of SEQ ID NO: 7 comprising a substitution, deletion, and/or insertion at one or more positions; and c. a fragment of the polypeptide of (a) or (b) that has DNase activity;

34. Composition according to any of paragraphs 32-33, wherein the polypeptide is having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, to the mature polypeptide of SEQ ID NO: 3, to the mature polypeptide of SEQ ID NO: 5, to the mature polypeptide of SEQ ID NO: 6, to the mature polypeptide of SEQ ID NO: 7 or, to the mature polypeptide of SEQ ID NO: 8.

35. Composition according to any of paragraphs 32-34, wherein the polypeptide comprises or consists of SEQ ID NO: 2 or the mature polypeptide of SEQ ID NO: 2, the polypeptide comprises or consists of SEQ ID NO: 3 or the mature polypeptide of SEQ ID NO: 3, the polypeptide comprises or consists of SEQ ID NO: 5 or the mature polypeptide of SEQ ID NO: 5, the polypeptide comprises or consists of SEQ ID NO: 6 or the mature polypeptide of SEQ ID NO: 6, the polypeptide comprises or consists of SEQ ID NO: 7 or the mature polypeptide of SEQ ID NO: 7 or the polypeptide comprises or consists of SEQ ID NO: 8 or the mature polypeptide of SEQ ID NO: 8.

36. Composition according to any of paragraphs 32-35, wherein the mature polypeptide is amino acids 1 to 206 of SEQ ID NO: 2, amino acids 1 to 206 of SEQ ID NO: 3, amino acids 1 to 188 of SEQ ID NO: 5, amino acids 1 to 110 of SEQ ID NO: 6 or amino acids 1 to 109 of SEQ ID NO: 7 or amino acids 1 to 206 of SEQ ID NO: 8.

37. Composition according to any of paragraphs 32-36, wherein the polypeptide is a variant of the mature polypeptide of SEQ ID NO: 2, SEQ ID NO: 3, SEQ ID NO: 5, SEQ ID NO: 6, SEQ ID NO: 7 or SEQ ID NO: 8, wherein the variant comprises a substitution, deletion, and/or insertion at one or more positions or a variant of the mature polypeptide of SEQ ID NO: 2, SEQ ID NO: 3, SEQ ID NO: 5, SEQ ID NO: 6 SEQ ID NO: 7 or SEQ ID NO: 8 which comprises a substitution, deletion, and/or insertion at one or more positions.

38. Composition according to any of paragraphs 32-37, wherein the polypeptide is a fragment of SEQ ID NO: 2, SEQ ID NO: 3, SEQ ID NO: 5, SEQ ID NO: 6, SEQ ID NO: 7 or SEQ ID NO: 8, wherein the fragment has DNase activity.

39. Composition according to any of the preceding composition paragraphs, for use for removing static electricity from a surface.

40. Composition according to paragraph 39, wherein the surface is a textile surface or a hard surface.

41. Composition according to paragraph 40, wherein the textile is made of synthetic fibers, such as polyester, polyamide, nylon, elastane (Spandex, Lycra), polyamide, fleece (Polyethylene terephthalate (PET)) or mixtures thereof.

42. Composition according to any of the preceding composition paragraphs, wherein the composition is a bar, a homogenous tablet, a tablet having two or more layers, a pouch having one or more compartments, a regular or compact powder, a granule, a paste, a gel, or a regular, compact or concentrated liquid or the composition is comprised on a sheet or wipe.

43. Composition according to any of the preceding composition paragraphs, wherein the composition is a liquid detergent, a powder detergent or a granule detergent.

44. A method for preventing, reducing or removing the static electricity of an item comprising the steps of:
a. Contacting an item to a composition according to any of paragraphs 20-43 and 67-81, a wipe according to any of paragraphs 82-90 or to a liquid solution comprising a polypeptide having DNase activity; and
b. Optionally rinsing the item,
wherein the item is a textile or a hard surface.

45. Method according to paragraph 44, wherein the method further comprises washing the item with the composition, the wipe or the liquid solution.

46. Method according to paragraph 44, wherein the method further comprises drying the item 47. Method according to any of the preceding method paragraphs, wherein the liquid solution further comprises antistatic agents, surfactants, builders, flocculating aid, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, bacteriocides, fungicides and/or pigments.

48. Method according to any of the preceding method paragraphs, wherein the liquid solution further comprises one or more enzymes selected from the group consisting of proteases, lipases, cutinases, amylases, carbohydrases, cellulases, pectinases, mannanases, arabinases, galactanases, xylanases and oxidases.

49. Method according to any of the preceding method paragraphs, wherein the pH of the liquid solution is in the range of 1 to 11.

50. Method according to any of the preceding method paragraphs, wherein the pH of the liquid solution is in the range 5.5 to 11, such as in the range of 7 to 9, in the range of 7 to 8 or in the range of 7 to 8.5.

51. Method according to any of the preceding method paragraphs, wherein the temperature of the liquid solution is in the range of 5° C. to 95° C., or in the range of 10° C. to 80° C., in the range of 10° C. to 70° C., in the range of 10° C. to 60° C., in the range of 10° C. to 50° C., in the range of 15° C. to 40° C. or in the range of 20° C. to 30° C.

52. Method according to any of the preceding method paragraphs, wherein the temperature of the liquid solution is 30° C.

53. Method according to any of the preceding method paragraphs, wherein the item is rinsed after being contacted to the liquid solution.

54. Method according to any of the preceding method paragraphs, wherein the item is rinsed with water or with water comprising a conditioner.

55. Method according to any of the preceding method paragraphs, wherein the polypeptide having DNase activity is of animal, vegetable or microbial origin.

56. Method according to paragraph 55, wherein the polypeptide is of human origin.

57. Method according to paragraph 55, wherein the polypeptide is obtained from mung bean.

58. Method according to paragraph 55, wherein the polypeptide is of bacterial or fungal origin.
59. Method according to paragraph 58, wherein the polypeptide is of fungal origin and the polypeptide is selected from the group consisting of:
   a. a polypeptide having at least 60% sequence identity to the mature polypeptide of SEQ ID NO: 2, a polypeptide having at least 60% sequence identity to the mature polypeptide of SEQ ID NO: 3, a polypeptide having at least 60% sequence identity to the mature polypeptide of SEQ ID NO: 5 or a polypeptide having at least 60% sequence identity to the mature polypeptide of SEQ ID NO: 8;
   b. a polypeptide encoded by a polynucleotide that hybridizes under low stringency conditions with
      i. the mature polypeptide coding sequence of SEQ ID NO: 1 or the mature polypeptide coding sequence of SEQ ID NO: 4
      ii. the cDNA sequence thereof, or
      iii. the full-length complement of (i) or (ii);
   c. a polypeptide encoded by a polynucleotide having at least 60% sequence identity to the mature polypeptide coding sequence of SEQ ID NO: 1 or the cDNA sequence thereof or a polypeptide encoded by a polynucleotide having at least 60% sequence identity to the mature polypeptide coding sequence of SEQ ID NO: 4 or the cDNA sequence thereof;
   d. a variant of the mature polypeptide of SEQ ID NO: 2 comprising a substitution, deletion, and/or insertion at one or more positions, a variant of the mature polypeptide of SEQ ID NO: 3 comprising a substitution, deletion, and/or insertion at one or more positions, a variant of the mature polypeptide of SEQ ID NO: 5 comprising a substitution, deletion, and/or insertion at one or more positions or a variant of the mature polypeptide of SEQ ID NO: 8 comprising a substitution, deletion, and/or insertion at one or more positions; and
   e. a fragment of the polypeptide of (a), (b), (c), or (d) that has DNase activity;
60. Method according to paragraph 58, wherein the polypeptide is of bacterial origin and the polypeptide is selected from the group consisting of:
   a. a polypeptide having at least 60% sequence identity to the mature polypeptide of SEQ ID NO: 6 or a polypeptide having at least 60% sequence identity to the mature polypeptide of SEQ ID NO: 7;
   b. a variant of the mature polypeptide of SEQ ID NO: 6 comprising a substitution, deletion, and/or insertion at one or more positions or a variant of the mature polypeptide of SEQ ID NO: 7 comprising a substitution, deletion, and/or insertion at one or more positions; and
   c. a fragment of the polypeptide of (a) or (b) that has DNase activity;
61. Method according to any of paragraphs 59-60, wherein the polypeptide is having at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2, to the mature polypeptide of SEQ ID NO: 3, to the mature polypeptide of SEQ ID NO: 5, to the mature polypeptide of SEQ ID NO: 6, to the mature polypeptide of SEQ ID NO: 7 or to the mature polypeptide of SEQ ID NO: 8.
62. Method according to any of paragraphs 59-61, wherein the polypeptide comprises or consists of SEQ ID NO: 2 or the mature polypeptide of SEQ ID NO: 2, the polypeptide comprises or consists of SEQ ID NO: 3 or the mature polypeptide of SEQ ID NO: 3, the polypeptide comprises or consists of SEQ ID NO: 5 or the mature polypeptide of SEQ ID NO: 5, the polypeptide comprises or consists of SEQ ID NO: 6 or the mature polypeptide of SEQ ID NO: 6, the polypeptide comprises or consists of SEQ ID NO: 7 or the mature polypeptide of SEQ ID NO: 7 or the polypeptide comprises or consists of SEQ ID NO: 8 or the mature polypeptide of SEQ ID NO: 8.
63. Method according to any of paragraphs 59-62, wherein the mature polypeptide is amino acids 1 to 206 of SEQ ID NO: 2, amino acids 1 to 206 of SEQ ID NO: 3, amino acids 1 to 188 of SEQ ID NO: 5, amino acids 1 to 110 of SEQ ID NO: 6, amino acids 1 to 109 of SEQ ID NO: 7 or amino acids 1 to 206 of SEQ ID NO: 8.
64. Method according to any of paragraphs 59-63, wherein the polypeptide is a variant of the mature polypeptide of SEQ ID NO: 2, SEQ ID NO: 3, SEQ ID NO: 5, SEQ ID NO: 6, SEQ ID NO: 7 or SEQ ID NO: 8, wherein the variant comprises a substitution, deletion, and/or insertion at one or more positions or a variant of the mature polypeptide of SEQ ID NO: 2, SEQ ID NO: 3, SEQ ID NO: 5, SEQ ID NO: 6, SEQ ID NO: 7 or SEQ ID NO: 8 which comprises a substitution, deletion, and/or insertion at one or more positions.
65. Method according to any of paragraphs 59-64, wherein the polypeptide is a fragment of SEQ ID NO: 2, SEQ ID NO: 3, SEQ ID NO: 5, SEQ ID NO: 6, SEQ ID NO: 7 or SEQ ID NO: 8, wherein the fragment has DNase activity.
66. Method according to any of the preceding method paragraphs, wherein the concentration of the polypeptide in is in the range of 0.00004-100 ppm enzyme protein, such as in the range of 0.00008-100, in the range of 0.0001-100, in the range of 0.0002-100, in the range of 0.0004-100, in the range of 0.0008-100, in the range of 0.001-100 ppm enzyme protein, in the range of 0.01-100 ppm enzyme protein, in the range of 0.05-50 ppm enzyme protein, in the range of 0.1-50 ppm enzyme protein, in the range of 0.1-30 ppm enzyme protein, in the range of 0.5-20 ppm enzyme protein or in the range of 0.5-10 ppm enzyme protein.
67. Composition according to any of paragraphs 20-43, wherein the composition is a liquid detergent composition, comprising a surfactant and a detergent builder in a total concentration of at least 3% by weight, and a detergent enzyme containing microcapsule, wherein the membrane of the microcapsule is produced by cross-linking of a polybranched polyamine having a molecular weight of more than 1 kDa.
68. Composition according to paragraph 67, wherein the reactive amino groups of the polybranched polyamine constitute at least 15% of the molecular weight.
69. Composition according to any of paragraphs 67-68, wherein the microcapsule is produced by using an acid chloride as crosslinking agent.
70. Composition according to any of paragraphs 67-69, wherein the diameter of the microcapsule is at least, or above, 50 micrometers.
71. Composition according to any of paragraphs 67-70, wherein the microcapsule contains at least 1% by weight of active enzyme.
72. Composition according to any of paragraphs 67-71, which further includes an alcohol, such as a polyol.

73. Composition according to any of paragraphs 67-72, wherein the surfactant is an anionic surfactant.
74. Composition according to any of paragraphs 67-73, which is a liquid laundry or automatic dishwash detergent composition.
75. Composition according to any of paragraphs 67-74, which contains less than 90% by weight of water.
76. Composition according to any of paragraphs 67-75, wherein the detergent enzyme is a polypeptide having DNase activity, protease, amylase, lipase, cellulase, mannanase, pectinase, or oxidoreductase.
77. Composition according to any of paragraphs 67-76, wherein the protease is a metalloprotease or an alkaline serine protease, such as a subtilisin.
78. Composition according to any of paragraphs 67-77, wherein the polypeptide having DNase activity is a polypeptide having at least 60% sequence identity to SEQ ID NO: 2, a polypeptide having at least 60% sequence identity to the mature polypeptide of SEQ ID NO: 3 or a polypeptide having at least 60% sequence identity to the mature polypeptide of SEQ ID NO: 5.
79. Detergent composition according to any of paragraphs 79-90, wherein the microcapsule is produced by interfacial polymerization using an acid chloride as crosslinking agent.
80. Detergent composition according to any of paragraphs 79-91, wherein the polybranched polyamine is a polyethyleneimine.
81. Detergent composition according to any of paragraphs 79-92, wherein the microcapsule comprises a source of Mg2+, Ca2+, or Zn2+ ions, such as a poorly soluble salt of Mg2+, Ca2+, or Zn2+.
82. A wipe for preventing, reducing or removing static electricity, which wipe comprises water and a polypeptide having DNase activity.
83. Wipe according to paragraph 82, wherein the wipe is impregnated or coated with the polypeptide having DNase activity.
84. Wipe according to any of paragraphs 82-83, wherein the wipe is made of textile or paper.
85. Wipe according to paragraph 84, wherein the textile is selected from the group consisting of cotton, flax/linen, jute, ramie, sisal, coir, viscose/rayon, cellulose acetate fibers (tricell), lyocell, wool, camel, cashmere, mohair, rabbit and silk, nylon, aramid, polyester, acrylic, polypropylene, spandex/elastane, microfibre or blends thereof
86. Wipe according to any of paragraphs 84-85, wherein the textile is a nonwoven textile or a spunlace textile.
87. Wipe according to any of paragraphs 84-86, wherein the wipe is made of microfiber,
88. Wipe according to paragraph 84, wherein the paper is tissue paper selected from the group consisting of hygienic tissue paper, facial tissue paper, paper towels, towelettes, toilet tissue, table napkins, kitchen roll, handkerchief and glass cleaning tissue paper.
89. Wipe according to any of paragraphs 82-88, wherein the wipe is a wet wipe.
90. Wipe according to paragraph 89, wherein the wipe comprises water, isopropyl alcohol and sodium laureth sulphate.
91. Wipe according to any of paragraphs 82-88, wherein the wipe is used for preventing, reducing or removing static electricity from surfaces.
92. Wipe according to paragraph 89, wherein the surface is present on screens, touch screens, phones, tablets, cameras, lenses, jewelry, glasses, fitness equipment or CD's.
93. An item for preventing, reducing or removing static electricity, which item comprises water and a polypeptide having DNase activity.

Assays and Detergent Compositions

Detergent Compositions

The below mentioned detergent composition can be used in combination with the polypeptide of the invention for preventing or reducing static electricity.

Composition of Ariel Sensitive White & Color, Liquid Detergent Composition:

Aqua, Alcohol Ethoxy Sulfate, Alcohol Ethoxylate, Amino Oxide, Citrid Acid, C12-18 topped palm kernel fatty acid, Protease, Glycosidase, Amylase, Ethanol, 1,2 Propanediol, Sodium Formate, Calcium Chloride, Sodium hydroxide, Silicone Emulsion, Trans-sulphated EHDQ (the ingredients are listed in descending order).

Composition of WFK IEC-A Model Detergent (Powder)

Ingredients: Linear sodium alkyl benzene sulfonate 8.8%, Ethoxylated fatty alcohol C12-18 (7 EO) 4.7%, Sodium soap 3.2%, Anti foam DC2-4248S 3.9%, Sodium aluminium silicate zeolite 4A 28.3%, Sodium carbonate 11.6%, Sodium salt of a copolymer from acrylic and maleic acid (Sokalan CP5) 2.4%, Sodium silicate 3.0%, Carboxymethylcellulose 1.2%, Dequest 2066 2.8%, Optical whitener 0.2%, Sodium sulfate 6.5%, Protease 0.4%.

Composition of Model Detergent A (Liquid)

Ingredients: 12% LAS, 11% AEO Biosoft N25-7 (NI), 7% AEOS (SLES), 6% MPG (monopropylene glycol), 3% ethanol, 3% TEA, 2.75% cocoa soap, 2.75% soya soap, 2% glycerol, 2% sodium hydroxide, 2% sodium citrate, 1% sodium formate, 0.2% DTMPA and 0.2% PCA (all percentages are w/w)

Composition of Ariel Actilift (Liquid)

Ingredients: 5-15% Anionic surfactants; <5% Non-ionic surfactants, Phosphonates, Soap; Enzymes, Optical brighteners, Benzisothiazolinone, Methylisothiazolinone, Perfumes, Alpha-isomethyl ionone, Citronellol, Geraniol, Linalool.

Composition of Ariel Actilift Colour & Style

Aqua, Sodium Dodecylbenzenesulfonate, C14-C15 Pareth-7, Sodium Citrate, Propylene Glycol, Sodium Palm Kernelate, Sodium Laureth Sulfate, MEA Dodecybenzenesulfonage, Sulfated Ethoxylated Hexamethylenediamine Quaternized, Sodium Cumenesulfonate, Perfume, Co-polymer of PEG/Vinyl Acetate, Sodium formate, Hydrogenated Castor Oil, Sodium Diethylenetriamine Pentamethylene Phosphonate, PEG/PPG-10/2 Propylheptyl Ether, Butyophenyl Methylpropional, Polyvinylpyridine-N-Oxide, Sorbitol, Glycerin, Ethanolamine, Sodium Hydroxide, Alpha-Isomethyl Ionone, Protease, Calcium Chloride, Geraniol, Linalool, Citronellol, Tripropylene Glycol, Glycosidase, Benzisothiazolinone, Dimethicone, Glycosidase, Sodium Acetate, Cellulase, Colorant, Glyceryl Stearate, Hydroxyethylcellulose, Silica.

Composition of Ariel Actilift Colour & Style, New Pack

Ingredients: Aqua, Sodium Laureth Sulfate, Propylene Glycol, C14-C15 Pareth-7, Sodium citrate, Sodium Palm Kernelate, Alcohol, Sodium Formate, Sulfated Ethoxylated Hexamethylenediamine Quaternized, Sodium Hydroxide, Perfume, Polyvinylpyridine-N-Oxide, Sorbitol, Calcium Chloride, protease, Glycerin, Glucosidase, Glycosidase, Sodium Acetate, Colorant, Cellulase.

Composition of Ariel Actilift Whites & Colours Coolclean, New Pack

Ingredients: Aqua, Sodium Laureth Sulfate, Propylene Glycol, C14-C15 Pareth-7, Sodium citrate, Sodium Palm Kernelate, Alcohol, Sodium Formate, Sulfated Ethoxylated Hexamethylenediamine Quaternized, Sodium Hydroxide, Perfume, Sorbitol, Calcium Chloride, protease, Glycerin, Glucosidase, Glycosidase, Sodium Acetate, Colorant, Cellulase.

Composition of Ariel Sensitive White & Color

Ingredients: Aqua, Sodium Laureth Sulfate, Propylene Glycol, C14-C15 Pareth-7, Sodium citrate, Sodium Palm Kernelate, Alcohol, Sodium Formate, Sulfated Ethoxylated Hexamethylenediamine Quaternized, Sodium Hydroxide, Sorbitol, Calcium Chloride, protease, Glycerin, Glycosidase, Sodium Acetate, Cellulase, Silica.

Composition of Ariel Actilift, Regular

Aqua, Sodium Dodecylbenzenesulfonate, C14-C15 Pareth-7, Sodium Citrate, Propylene Glycol, Sodium Palm Kernelate, Sodium Laureth Sulfate, MEA Dodecylbenzenesulfonage, Sulfated Ethoxylated Hexamethylenediamine Quaternized, Sodium Cumenesulfonate, Perfume, Co-polymer of PEG/Vinyl Acetate, Sodium formate, C12-C14 Pareth-7, Hydrogenated Castor Oil, Sodium Diethylenetriamine Pentamethylene Phosphonate, PEG/PPG-10/2 Propylheptyl Ether, Butyophenyl Methylpropional, Fluorescent Brightener 9, Sorbitol, Glycerin, Ethanolamine, Sodium Hydroxide, Alpha-Isomethyl Ionone, Protease, Calcium Chloride, Geraniol, Linalool, Citronellol, Tripropylene Glycol, Sodium Chloride, Glycosidase, Benzisothiazolinone, Dimethicone, Glycosidase, Sodium Acetate, Cellulase, Colorant, Glyceryl Stearate, Hydroxyethylcellulose, Silica.

Composition of Persil Small & Mighty (Liquid)

Ingredients: 15-30% Anionic surfactants, Non-ionic surfactants, 5-15% Soap, <5% Polycarboxylates, Perfume, Phosphates, Optical Brighteners Composition of Fairy Non Bio (Liquid)

Ingredients: 15-30% Anionic Surfactants, 5-15% Non-Ionic Surfactants, Soap, Benzisothiazolinone, Methylisothiazolinone, Perfumes Composition of Model Detergent T (Powder)

Ingredients: 11% LAS, 2% AS/AEOS, 2% soap, 3% AEO, 15.15% sodium carbonate, 3% sodium silicate, 18.75% zeolite, 0.15% chelant, 2% sodium citrate, 1.65% AA/MA copolymer, 2.5% CMC and 0.5% SRP (all percentages are w/w).

Composition of Model Detergent X (Powder)

Ingredients: 16.5% LAS, 15% zeolite, 12% sodium disilicate, 20% sodium carbonate, 1% sokalan, 35.5% sodium sulfate (all percentages are w/w).

Composition of Ariel Actilift (Powder)

Ingredients: 15-30% Anionic surfactants, <5% Non-ionic surfactants, Phosphonates, Polycarboxylates, Zeolites; Enzymes, Perfumes, Hexyl cinnamal.

Composition of Persil Megaperls (Powder)

Ingredients: 15-30% of the following: anionic surfactants, oxygen-based bleaching agent and zeolites, less than 5% of the following: non-ionic surfactants, phosphonates, polycarboxylates, soap, Further ingredients: Perfumes, Hexyl cinnamal, Benzyl salicylate, Linalool, optical brighteners, Enzymes and Citronellol.

Gain Liquid, Original:

Ingredients: Water, Alcohol Ethoxysulfate, Diethylene Glycol, Alcohol Ethoxylate, Ethanolamine, Linear Alkyl Benzene Sulfonate, Sodium Fatty Acids, Polyethyleneimine Ethoxylate, Citric Acid, Borax, Sodium Cumene Sulfonate, Propylene Glycol, DTPA, Disodium Diaminostilbene Disulfonate, Dipropylethyl Tetraamine, Sodium Hydroxide, Sodium Formate, Calcium Formate, Dimethicone, Amylase, Protease, Liquitint™, Hydrogenated Castor Oil, Fragrance Tide Liquid, Original:

Ingredients: Linear alkylbenzene sulfonate, propylene glycol, citric acid, sodium hydroxide, borax, ethanolamine, ethanol, alcohol sulfate, polyethyleneimine ethoxylate, sodium fatty acids, diquaternium ethoxysulfate, protease, diethylene glycol, laureth-9, alkyldimethylamine oxide, fragrance, amylase, disodium diaminostilbene disulfonate, DTPA, sodium formate, calcium formate, polyethylene glycol 4000, mannanase, Liquitint™ Blue, dimethicone.

Liquid Tide, Free and Gentle:

Water, sodium alcoholethoxy sulfate, propylene glycol, borax, ethanol, linear alkylbenzene sulfonate sodium, salt, polyethyleneimine ethoxylate, diethylene glycol, trans sulfated & ethoxylated hexamethylene diamine, alcohol ethoxylate, linear alkylbenzene sulfonate, MEA salt, sodium formate, sodium alkyl sulfate, DTPA, amine oxide, calcium formate, disodium diaminostilbene, disulfonate, amylase, protease, dimethicone, benzisothiazolinone.

Tide Coldwater Liquid, Fresh Scent:

Water, alcoholethoxy sulfate, linear alkylbenzene sulfonate, diethylene glycol, propylene glycol, ethanolamine, citric acid, Borax, alcohol sulfate, sodium hydroxide, polyethyleneimine, ethoxylate, sodium fatty acids, ethanol, protease, Laureth-9, diquaternium ethoxysulfate, lauramine oxide, sodium cumene, sulfonate, fragrance, DTPA, amylase, disodium, diaminostilbene, disulfonate, sodium formate, disodium distyrylbiphenyl disulfonate, calcium formate, polyethylene glycol 4000, mannanase, pectinase, Liquitint™ Blue, dimethicone.

Tide TOTALCARE™ Liquid, Cool Cotton:

Water, alcoholethoxy sulfate, propylene glycol, sodium fatty acids, laurtrimonium chloride, ethanol, sodium hydroxide, sodium cumene sulfonate, citric acid, ethanolamine, diethylene glycol, silicone polyether, borax, fragrance, polyethyleneimine ethoxylate, protease, Laureth-9, DTPA, polyacrylamide quaternium chloride, disodium diaminostilbene disulfonate, sodium formate, Liquitint™ Orange, dipropylethyl tetraamine, dimethicone, cellulase, Liquid Tide Plus Bleach Alternative™, Vivid White and Bright, Original and Clean Breeze:

Water, sodium alcoholethoxy sulfate, sodium alkyl sulfate, MEA citrate, linear alkylbenzene sulfonate, MEA salt, propylene glycol, diethylene glycol, polyethyleneimine ethoxylate, ethanol, sodium fatty acids, ethanolamine, lauramine oxide, borax, Laureth-9, DTPA, sodium cumene sulfonate, sodium formate, calcium formate, linear alkylbenzene sulfonate, sodium salt, alcohol sulfate, sodium hydroxide, diquaternium ethoxysulfate, fragrance, amylase, protease, mannanase, pectinase, disodium diaminostilbene disulfonate, benzisothiazolinone, Liquitint™ Blue, dimethicone, dipropylethyl tetraamine.

Liquid Tide HE, Original Scent:

Water, Sodium alcoholethoxy sulfate, MEA citrate, Sodium Alkyl Sulfate, alcohol ethoxylate, linear alkylbenzene sulfonate, MEA salt, sodium fatty acids, polyethyleneimine ethoxylate, diethylene glycol, propylene glycol, diquaternium ethoxysulfate, borax, polyethyleneimine, ethoxylate propoxylate, ethanol, sodium cumene sulfonate, fragrance, DTPA, disodium diaminostilbene disulfonate, Mannanase, cellulase, amylase, sodium formate, calcium formate, Lauramine oxide, Liquitint™ Blue, Dimethicone/polydimethyl silicone.

Tide TOTALCARE HE Liquid, renewing Rain:

Water, alcoholethoxy sulfate, linear alkylbenzene sulfonate, alcohol ethoxylate, citric acid, Ethanolamine, sodium fatty acids, diethylene glycol, propylene glycol, sodium hydroxide, borax, polyethyleneimine ethoxylate, silicone polyether, ethanol, protease, sodium cumene sulfonate, diquaternium ethoxysulfate, Laureth-9, fragrance, amylase, DTPA, disodium diaminostilbene disulfonate, disodium distyrylbiphenyl disulfonate, sodium formate, calcium formate, mannanase, Liquitint™ Orange, dimethicone, polyacrylamide quaternium chloride, cellulase, dipropylethyl tetraamine.

Tide liquid HE Free:
Water, alcoholethoxy sulfate, diethylene glycol, monoethanolamine citrate, sodium formate, propylene glycol, linear alkylbenzene sulfonates, ethanolamine, ethanol, polyethyleneimine ethoxylate, amylase, benzisothiazolin, borax, calcium formate, citric acid, diethylenetriamine pentaacetate sodium, dimethicone, diquaternium ethoxysulfate, disodium diaminostilbene disulfonate, Laureth-9, mannanase, protease, sodium cumene sulfonate, sodium fatty acids.

Tide Coldwater HE Liquid, Fresh Scent:
Water, alcoholethoxy sulfate, MEA Citrate, alcohol sulfate, Alcohol ethoxylate, Linear alkylbenzene sulfonate MEA, sodium fatty acids, polyethyleneimine ethoxylate, diethylene glycol, propylene glycol, diquaternium ethoxysulfate, borax, polyethyleneimine ethoxylate propoxylate, ethanol, sodium cumene sulfonate, fragrance, DTPA, disodium diaminostilbene disulfonate, protease, mannanase, cellulase, amylase, sodium formate, calcium formate, lauramine oxide, Liquitint™ Blue, dimethicone.

Tide for Coldwater HE Free Liquid:
Water, sodium alcoholethoxy sulfate, MEA Citrate, Linear alkylbenzene sulfonate: sodium salt, Alcohol ethoxylate, Linear alkylbenzene sulfonate: MEA salt, sodium fatty acids, polyethyleneimine ethoxylate, diethylene glycol, propylene glycol, diquaternium ethoxysulfate, Borax, protease, polyethyleneimine ethoxylate propoxylate, ethanol, sodium cumene sulfonate, Amylase, citric acid, DTPA, disodium diaminostilbene disulfonate, sodium formate, calcium formate, dimethicone.

Tide Simply Clean & Fresh:
Water, alcohol ethoxylate sulfate, linear alkylbenzene sulfonate Sodium/Mea salts, propylene glycol, diethylene glycol, sodium formate, ethanol, borax, sodium fatty acids, fragrance, lauramine oxide, DTPA, Polyethylene amine ethoxylate, calcium formate, disodium diaminostilbene disulfonate, dimethicone, tetramine, Liquitint™ Blue.

Tide Pods, Ocean Mist, Mystic Forest, Spring Meadow:
Linear alkylbenzene sulfonates, C12-16 Pareth-9, propylene glycol, alcoholethoxy sulfate, water, polyethyleneimine ethoxylate, glycerine, fatty acid salts, PEG-136 polyvinyl acetate, ethylene Diamine disuccinic salt, monoethanolamine citrate, sodium bisulfite, diethylenetriamine pentaacetate sodium, disodium distyrylbiphenyl disulfonate, calcium formate, mannanase, exyloglucanase, sodium formate, hydrogenated castor oil, natalase, dyes, termamyl, subtilisin, benzisothiazolin, perfume.

Tide to Go:
Deionized water, Dipropylene Glycol Butyl Ether, Sodium Alkyl Sulfate, Hydrogen Peroxide, Ethanol, Magnesium Sulfate, Alkyl Dimethyl Amine Oxide, Citric Acid, Sodium Hydroxide, Trimethoxy Benzoic Acid, Fragrance.

Tide Stain Release Liquid:
Water, Alkyl Ethoxylate, Linear Alkylbenzenesulfonate, Hydrogen Peroxide, Diquaternium Ethoxysulfate, Ethanolamine, Disodium Distyrylbiphenyl Disulfonate, tetrabutyl Ethylidinebisphenol, F&DC Yellow 3, Fragrance.

Tide Stain Release Powder:
Sodium percarbonate, sodium sulfate, sodium carbonate, sodium aluminosilicate, nonanoyloxy benzene sulfonate, sodium polyacrylate, water, sodium alkylbenzenesulfonate, DTPA, polyethylene glycol, sodium palmitate, amylase, protease, modified starch, FD&C Blue 1, fragrance.

Tide Stain Release, Pre Treater Spray:
Water, Alkyl Ethoxylate, MEA Borate, Linear Alkylbenzenesulfonate, Propylene Glycol, Diquaternium Ethoxysulfate, Calcium Chlorideenzyme, Protease, Ethanolamine, Benzoisothiazolinone, Amylase, Sodium Citrate, Sodium Hydroxide, Fragrance.

Tide to Go Stain Eraser:
Water, Alkyl Amine Oxide, Dipropylene Glycol Phenyl Ether, Hydrogen Peroxide, Citric Acid, Ethylene Diamine Disuccinic Acid Sodium salt, Sodium Alkyl Sulfate, Fragrance.

Tide boost with Oxi:
Sodium bicarbonate, sodium carbonate, sodium percarbonate, alcohol ethoxylate, sodium chloride, maleic/acrylic copolymer, nonanoyloxy benzene sulfonate, sodium sulfate, colorant, diethylenetriamine pentaacetate sodium salt, hydrated aluminosilicate (zeolite), polyethylene glycol, sodium alkylbenzene sulfonate, sodium palmitate, starch, water, fragrance.

Tide Stain Release Boost Duo Pac:
Polyvinyl Alcohol pouch film, wherein there is packed a liquid part and a powder part:
Liquid Ingredients:
Dipropylene Glycol, diquaternium Ethoxysulfate, Water, Glycerin, Liquitint™ Orange, Powder Ingredients: sodium percarbonate, nonanoyloxy benzene sulfonate, sodium carbonate, sodium sulfate, sodium aluminosilicate, sodium polyacrylate, sodium alkylbenzenesulfonate, maleic/acrylic copolymer, water, amylase, polyethylene glycol, sodium palmitate, modified starch, protease, glycerine, DTPA, fragrance.

Tide Ultra Stain Release:
Water, sodium alcoholethoxy sulfate, linear alkyl benzene sulfonate, sodium/MEA salts, MEA citrate, propylene glycol, polyethyleneimine ethoxylate, ethanol, diethylene glycol, polyethyleneimine propoxyethoxylate, sodium fatty acids, protease, borax, sodium cumene sulfonate, DTPA, fragrance, amylase, disodium diaminostilbene disulfonate, calcium formate, sodium formate, gluconase, dimethicone, Liquitint™ Blue, mannanase.

Ultra Tide with a Touch of Downy® Powdered Detergent, April Fresh/Clean Breeze/April Essence:
Sodium Carbonate, Sodium Aluminosilicate, Sodium Sulfate, Linear Alkylbenzene Sulfonate, Bentonite, Water, Sodium Percarbonate, Sodium Polyacrylate, Silicate, Alkyl Sulfate, Nonanoyloxybenzenesulfonate, DTPA, Polyethylene Glycol 4000, Silicone, Ethoxylate, fragrance, Polyethylene Oxide, Palmitic Acid, Disodium Diaminostilbene Disulfonate, Protease, Liquitint™ Red, FD&C Blue 1, Cellulase.

Ultra Tide with a Touch of Downy Clean Breeze:
Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimine, propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, sodium formate, Liquitint™ Blue.

Ultra Tide with Downy Sun Blossom:
Water, sodium alcoholethoxy sulfate, MEA citrate, linear alkyl benzene sulfonate: sodium/MEA salts, propylene glycol, ethanol, diethylene glycol, polyethyleneimine propoxyethoxylate, polyethyleneimine ethoxylate, alcohol sulfate, dimethicone, fragrance, borax, sodium fatty acids, DTPA, protease, sodium bisulfite, disodium diaminostilbene disulfonate, amylase, castor oil, calcium formate, MEA, styrene acrylate copolymer, propanaminium propanamide, gluconase, sodium formate, Liquitint™ Blue.

Ultra Tide with Downy April Fresh/Sweet Dreams:

Water, sodium alcoholethoxy sulfate, MEA citrate, linear alkyl benzene sulfonate: sodium/MEA salts, propylene glycol, polyethyleneimine ethoxylate, ethanol, diethylene glycol, polyethyleneimin propoxyethoxylate, diquaternium ethoxysulfate, alcohol sulfate, dimethicone, fragrance, borax, sodium fatty acids, DTPA, protease, sodium bisulfite, disodium diaminostilbene disulfonate, amylase, gluconase, castor oil, calcium formate, MEA, styrene acrylate copolymer, propanaminium propanamide, sodium formate, Liquitint™ Blue.

Ultra Tide Free Powdered Detergent:

Sodium Carbonate, Sodium Aluminosilicate, Alkyl Sulfate, Sodium Sulfate, Linear Alkylbenzene Sulfonate, Water, Sodium polyacrylate, Silicate, Ethoxylate, Sodium percarbonate, Polyethylene Glycol 4000, Protease, Disodium Diaminostilbene Disulfonate, Silicone, Cellulase.

Ultra Tide Powdered Detergent, Clean Breeze/Spring Lavender/mountain Spring:

Sodium Carbonate, Sodium Aluminosilicate, Sodium Sulfate, Linear Alkylbenzene Sulfonate, Alkyl Sulfate, Sodium Percarbonate, Water, Sodium Polyacrylate, Silicate, Nonanoyloxybenzenesulfonate, Ethoxylate, Polyethylene Glycol 4000, Fragrance, DTPA, Disodium Diaminostilbene Disulfonate, Palmitic Acid, Protease, Silicone, Cellulase.

Ultra Tide HE (High Efficiency) Powdered Detergent, Clean Breeze:

Sodium Carbonate, Sodium Aluminosilicate, Sodium Sulfate, Linear Alkylbenzene Sulfonate, Water, Nonanoyloxybenzenesulfonate, Alkyl Sulfate, Sodium Polyacrylate, Silicate, Sodium Percarbonate, Ethoxylate, Polyethylene Glycol 4000, Fragrance, DTPA, Palmitic Acid, Disodium Diaminostilbene Disulfonate, Protease, Silicone, Cellulase.

Ultra Tide Coldwater Powdered Detergent, Fresh Scent:

Sodium Carbonate, Sodium Aluminosilicate, Sodium Sulfate, Sodium Percarbonate, Alkyl Sulfate, Linear Alkylbenzene Sulfonate, Water, Nonanoyloxybenzenesulfonate, Sodium Polyacrylate, Silicate, Ethoxylate, Polyethylene Glycol 4000, DTPA, Fragrance, Natalase, Palmitic Acid, Protease, Disodium, Diaminostilbene Disulfonate, FD&C Blue 1, Silicone, Cellulase, Alkyl Ether Sulfate.

Ultra Tide with Bleach Powdered Detergent, Clean Breeze:

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate, Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

Ultra Tide with Febreeze Freshness™ Powdered Detergent, Spring Renewal:

Sodium Carbonate, Sodium Aluminosilicate, Sodium Sulfate, Linear Alkylbenzene Sulfonate, Sodium Percarbonate, Alkyl Sulfate, Water, Sodium Polyacrylate, Silicate, Nonanoyloxybenzenesulfonate, Ethoxylate, Polyethylene Glycol 4000, DTPA, Fragrance, Cellulase, Protease, Disodium Diaminostilbene Disulfonate, Silicone, FD&C Blue 1.

Liquid Tide Plus with Febreeze Freshness—Sport HE Active Fresh:

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, Ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Plus Febreeze Freshness Spring & Renewal:

Water, sodium alcoholethoxy sulfate, linear alkyl benzene sulfonate: sodium/MEA salts, MEA citrate, propylene glycol, polyethyleneimine ethoxylate, fragrance, ethanol, diethylene glycol, polyethyleneimine propoxyethoxylate, protease, alcohol sulfate, borax, sodium fatty acids, DTPA, disodium diaminostilbene disulfonate, MEA, mannanase, gluconase, sodium formate, dimethicone, Liquitint™ Blue, tetramine.

Liquid Tide Plus with Febreeze Freshness, Sport HE Victory Fresh:

Water, Sodium alcoholethoxy sulfate, MEA citrate, linear alkylbenzene sulfonate, sodium salt, linear alkylbenzene sulfonate: MEA salt, alcohol ethoxylate, sodium fatty acids, propylene glycol, diethylene glycol, polyethyleneimine ethoxylate propoxylate, diquaternium ethoxysulfate, ethanol, sodium cumene sulfonate, borax, fragrance, DTPA, Sodium bisulfate, disodium diaminostilbene disulfonate, Mannanase, cellulase, amylase, sodium formate, calcium formate, Lauramine oxide, Liquitint™ Blue, Dimethicone/polydimethyl silicone.

Tide Vivid White+Bright Powder, Original:

Sodium Carbonate, Sodium Aluminosilicate, Sodium Sulfate, Linear Alkylbenzene Sulfonate, Sodium Percarbonate, Nonanoyloxybenzenesulfonate, Alkyl Sulfate, Water, Silicate, Sodium Polyacrylate Ethoxylate, Polyethylene Glycol 4000, Fragrance, DTPA, Palmitic Acid, Protease, Disodium Diaminostilbene Disulfonate, Silicone, FD&C Blue 1, Cellulase, Alkyl Ether Sulfate.

HEY SPORT TEX WASH Detergent

Aqua, dodecylbenzenesulfonsäure, laureth-11, peg-75 lanolin, propylene glycol, alcohol denat., potassium soyate, potassium hydroxide, disodium cocoamphodiacetate, ethylendiamine triacetate cocosalkyl acetamide, parfum, zinc ricinoleate, sodium chloride, benzisothiazolinone, methylisothiazolinone, ci 16255, benzyl alcohol.

The products named Tide, Ariel, Gain and Fairy are commercially available products supplied by Procter & Gamble. The products named Persil are commercially available products supplied by Unilever and Henkel. The products named Hey Sport are commercially available products supplied by Hey Sport.

| Ingredient | Amount (in wt %) |
| --- | --- |
| Anionic detersive surfactant (such as alkyl benzene sulphonate, alkyl ethoxylated sulphate and mixtures | from 8 wt % to 15 wt % thereof) |
| Non-ionic detersive surfactant (such as alkyl ethoxylated alcohol) | from 0.5 wt % to 4 wt % |

-continued

| Ingredient | Amount (in wt %) |
|---|---|
| Cationic detersive surfactant (such as quaternary ammonium compounds) | from 0 to 4 wt % |
| Other detersive surfactant (such as zwiterionic detersive surfactants, amphoteric surfactants and mixtures thereof) | from 0 wt % to 4 wt % |
| Carboxylate polymer (such as co-polymers of maleic acid and acrylic acid) | from 1 wt % to 4 wt % |
| Polyethylene glycol polymer (such as a polyethylene glycol polymer comprising poly vinyl acetate side chains) | from 0.5 wt % to 4 wt % |
| Polyester soil release polymer (such as Repel-o-tex from and/or Texcare polymers) | 0.1 to 2 wt % |
| Cellulosic polymer (such as carboxymethyl cellulose, methyl cellulose and combinations thereof) | from 0.5 wt % to 2 wt % |
| Other polymer (such as amine polymers, dye transfer inhibitor polymers, hexamethylenediamine derivative polymers, and mixtures thereof) | from 0 wt % to 4 wt % |
| Zeolite builder and phosphate builder (such as zeolite 4A and/or sodium tripolyphosphate) | from 0 wt % to 4 wt % |
| Other builder (such as sodium citrate and/or citric acid) | from 0 wt % to 3 wt % |
| Carbonate salt (such as sodium carbonate and/or sodium bicarbonate) | from 15 wt % to 30 wt % |
| Silicate salt (such as sodium silicate) | from 0 wt % to 10 wt % |
| Filler (such as sodium sulphate and/or bio-fillers) | from 10 wt % to 40 wt % |
| Source of available oxygen (such as sodium percarbonate) | from 10 wt % to 20 wt % |
| Bleach activator (such as tetraacetylethylene diamine (TAED) and/or nonanoyloxybenzenesulphonate (NOBS) | from 2 wt % to 8 wt % |
| Bleach catalyst (such as oxaziridinium-based bleach catalyst and/or transition metal bleach catalyst) | from 0 wt % to 0.1 wt % |
| Other bleach (such as reducing bleach and/or pre- formed peracid) | from 0 wt % to 10 wt % |
| Chelant (such as ethylenediamine-N'N'-disuccinic acid (EDDS) and/or hydroxyethane diphosphonic acid(HEDP) | from 0.2 wt % to 1 wt % |
| Photobleach (such as zinc and/or aluminium sulphonated phthalocyanine) | from 0 wt % to 0.1 wt % |
| Hueing agent (such as direct violet 99, acid red 52, acid blue 80, direct violet 9, solvent violet 13 and any combination thereof) | from 0 wt % to 1 wt % |
| Brightener (such as brightener 15 and/or brightener 49) | from 0.1 wt % to 0.4 wt % |
| Protease (such as Savinase, Savinase Ultra, Purafect, FN3, FN4 and any combination thereof) | from 0.1 wt % to 0.4 wt % |
| Amylase (such as Termamyl, Termamyl ultra Natalase, Optisize, Stainzyme, Stainzyme Plus, and any combination thereof) | from 0.05 wt % to 0.2 wt % |
| Cellulase (such as Carezyme and/or Celluclean) | from 0.05 wt % to 0.2 wt % |
| Lipase (such as Lipex, Lipolex, Lipoclean and any combination thereof) | from 0.2 to 1 wt % |
| Other enzyme (such as xyloglucanase, cutinase, pectate lyase, mannanase, bleaching enzyme) | from 0 wt % to 2 wt % |
| Fabric softener (such as montmorillonite clay and/or polydimethylsiloxane (PDMS) | from 0 wt % to 4 wt % |
| Flocculant (such as polyethylene oxide) | from 0 wt % to 1 wt % |
| Suds suppressor (such as silicone and/or fatty acid) | from 0 wt % to 0.1 wt % |
| Perfume (such as perfume microcapsule, spray-on perfume, starch encapsulated perfume accords, perfume loaded zeolite, and any combination thereof) | from 0.1 wt % to 1 wt % |
| Aesthetics (such as coloured soap rings and/or coloured speckles/noodles) | from 0 wt % to 1 wt % |
| Miscellaneous | balance |

| Ingredient | Amount |
|---|---|
| Carboxyl group-containing polymer (comprising from about 60% to about 70% by mass of an acrylic acid-based monomer (A); and from about 30% to about 40%) by mass of a sulfonic acid group-containing monomer (B); and wherein the average molecular weight is from about 23,000 to about 50,000 preferably in the range of from about 25,000 to about 38,000 as described in WO2014032269. | from about 0.5 wt % to about 1.5 wt % |
| Amylase (Stainzyme Plus(R), having an enzyme activity of 14 mg active enzyme/g) | from about 0.1 wt % to about 0.5 wt % |

-continued

| Ingredient | Amount |
|---|---|
| Anionic detersive surfactant (such as alkyl benzene sulphonate, alkyl ethoxylated sulphate and mixtures thereof) | from about 8 wt % to about 15 wt % |
| Non-ionic detersive surfactant (such as alkyl ethoxylated alcohol) | from about 0.5 wt % to 4 wt % |
| Cationic detersive surfactant (such as quaternary ammonium compounds) | from about 0 wt % to about 4 wt % |
| Other detersive surfactant (such as zwiterionic detersive surfactants, amphoteric surfactants and mixtures thereof) | from about 0 wt % to 4 wt % |
| Carboxylate polymer (such as co-polymers of maleic acid and acrylic acid) | from about 1 wt % to about 4 wt % |
| Polyethylene glycol polymer (such as a polyethylene glycol polymer comprising poly vinyl acetate side chains) | from about 0 wt % to about 4 wt % |
| Polyester soil release polymer (such as Repel-O-Tex(R) and/or Texcare(R) polymers) | from about 0.1 wt % to about 2 wt % |
| Cellulosic polymer (such as carboxymethyl cellulose, methyl cellulose and combinations thereof) | from about 0.5 wt % to about 2 wt % |
| Other polymer (such as amine polymers, dye transfer inhibitor polymers, hexamethylenediamine derivative polymers, and mixtures thereof) | from about 0 wt % to about 4 wt % |
| Zeolite builder and phosphate builder (such as zeolite 4A and/or sodium tripolyphosphate) | from about 0 wt % to about 4 wt % |
| Other builder (such as sodium citrate and/or citric acid) | from about 0 wt % to about 3 wt % |
| Carbonate salt (such as sodium carbonate and/or sodium bicarbonate) | from about 15 t % to about 30 wt % |
| Silicate salt (such as sodium silicate) | from about 0 wt % to about 10 wt % |
| Filler (such as sodium sulphate and/or bio-fillers) | from about 10 wt % to about 40 wt % |
| Source of available oxygen (such as sodium percarbonate) | from about 10 wt % to about 20 wt % |
| Bleach activator (such as tetraacetylethylene diamine (TAED) and/or nonanoyloxybenzenesulphonate (NOBS) | from about 2 wt % to about 8 wt % |
| Bleach catalyst (such as oxaziridinium-based bleach catalyst and/or transition metal bleach catalyst) | from about 0 wt % to about 0.1 wt % |
| Other bleach (such as reducing bleach and/or pre formed peracid) | from about 0 wt % to about 10 wt % |
| Chelant (such as ethylenediamine-N'N'-disuccinic acid (EDDS) and/or hydroxyethane diphosphonic acid (HEDP) | from about 0.2 wt % to about 1 wt % |
| Photobleach (such as zinc and/or aluminium sulphonated phthalocyanine) | from about 0 wt % to about 0.1 wt % |
| Hueing agent (such as direct violet 99, acid red 52, acid blue 80, direct violet 9, solvent violet 13 and any combination thereof) | from about 0 wt % to about 0.5 wt % |
| Brightener (such as brightener 15 and/or brightener 49) | from about 0.1 wt % to about 0.4 wt % |
| Protease (such as Savinase, Polarzyme, Purafect, FN3, FN4 and any combination thereof, typically having an enzyme activity of from about 20 mg to about 100 mg active enzyme/g) | from about 0.1 wt % to about 1.5 wt % |
| Amylase (such as Termamyl(R), Termamyl Ultra(R), Natalase(R), Optisize HT Plus(R), Powerase(R), Stainzyme(R) and any combination thereof, typically having an enzyme activity of from about 10 mg to about 50 mg active enzyme/g) | from about 0.05 wt % to about 0.2 wt % |
| Cellulase (such as Carezyme(R), Celluzyme(R) and/or Celluclean(R), typically having an enzyme activity of about from 10 to 50 mg active enzyme/g) | from about 0.05 wt % to 0.5 wt % |
| Lipase (such as Lipex(R), Lipolex(R), Lipoclean(R) and any combination thereof, typically having an enzyme activity of from about 10 mg to about 50 mg active enzyme/g) | from about 0.2 wt % to about 1 wt % |
| Other enzyme (such as xyloglucanase (e.g., Whitezyme(R)), cutinase, pectate lyase, mannanase, bleaching enzyme, typically having an enzyme activity of from about 10 mg to about 50 mg active enzyme/g) | from 0 wt % to 2 wt % |
| Fabric softener (such as montmorillonite clay and/or polydimethylsiloxane (PDMS)) | from 0 wt % to 15 wt % |
| Flocculant (such as polyethylene oxide) | from 0 wt % to 1 wt % |
| Suds suppressor (such as silicone and/or fatty acid) | from 0 wt % to 0.1 wt % |

| Ingredient | Amount |
| --- | --- |
| Perfume (such as perfume microcapsule, spray-on perfume, starch encapsulated perfume accords,perfume loaded zeolite, and any combination thereof) | from 0.1 wt % to 1 wt % |
| Aesthetics (such as colored soap rings and/or colored speckles/noodles) | from 0 wt % to 1 wt % |
| Miscellaneous | Balance |

All enzyme levels expressed as rug active enzyme protein per 100 g detergent composition. Surfactant ingredients can be obtained from BASF, Ludwigshafen, Germany (Lutensol®); Shell Chemicals, London, UK; Stepan, Northfield, Ill., USA; Huntsman, Huntsman, Salt Lake City, Utah, USA; Clariant, Sulzbach, Germany (Praepagen®). Sodium tripolyphosphate can be obtained from Rhodia, Paris, France. Zeolite can be obtained from Industrial Zeolite (UK) Ltd, Grays, Essex, UK. Citric acid and sodium citrate can be obtained from Jungbunzlauer, Basel, Switzerland. NOBS is sodium nonanoyloxybenzenesulfonate, supplied by Eastman, Batesville, Ark., USA.

TAED is tetraacetylethylenediamine, supplied under the Peractive® brand name by Clariant GmbH, Sulzbach, Germany.

Sodium carbonate and sodium bicarbonate can be obtained from Solvay, Brussels, Belgium. Polyacrylate, polyacrylate/maleate copolymers can be obtained from BASF, Ludwigshafen, Germany.

Repel-O-Tex® can be obtained from Rhodia, Paris, France. Texcare® can be obtained from Clariant, Sulzbach, Germany. Sodium percarbonate and sodium carbonate can be obtained from Solvay, Houston, Tex., USA.

Na salt of Ethylenediamine-N,N'-disuccinic acid, (S,S) isomer (EDDS) was supplied by Octel, Ellesmere Port, UK. Hydroxy ethane di phosphonate (HEDP) was supplied by Dow Chemical, Midland, Mich., USA.

Enzymes Savinase®, Savinase® Ultra, Stainzyme® Plus, Lipex®, Lipolex®, Lipoclean®, Celluclean®, Carezyme®, Natalase®, Stainzyme®, Stainzyme® Plus, Termamyl®, Termamyl® ultra, and Mannaway® can be obtained from Novozymes, Bagsvaerd, Denmark. Enzymes Purafect®, FN3, FN4 and Optisize can be obtained from Genencor International Inc., Palo Alto, Calif., US. Direct violet 9 and 99 can be obtained from BASF DE, Ludwigshafen, Germany. Solvent violet 13 can be obtained from Ningbo Lixing Chemical Co., Ltd. Ningbo, Zhejiang, China. Brighteners can be obtained from Ciba Specialty Chemicals, Basel, Switzerland.

All percentages and ratios are calculated by weight unless otherwise indicated. All percentages and ratios are calculated based on the total composition unless otherwise indicated. It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Wash Assays

Launder-O-Meter (LOM) Model Wash System

The Launder-O-Meter (LOM) is a medium scale model wash system that can be applied to test up to 20 different wash conditions simultaneously. A LOM is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full scale experiments in front loader washing machines.

Mini Launder-O-Meter (MiniLOM) Model Wash System

MiniLOM is a modified mini wash system of the Launder-O-Meter (LOM), which is a medium scale model wash system that can be applied to test up to 20 different wash conditions simultaneously. A LOM or is basically a large temperature controlled water bath with 20 closed metal beakers rotating inside it. Each beaker constitutes one small washing machine and during an experiment, each will contain a solution of a specific detergent/enzyme system to be tested along with the soiled and unsoiled fabrics it is tested on. Mechanical stress is achieved by the beakers being rotated in the water bath and by including metal balls in the beaker.

The LOM model wash system is mainly used in medium scale testing of detergents and enzymes at European wash conditions. In a LOM experiment, factors such as the ballast to soil ratio and the fabric to wash liquor ratio can be varied. Therefore, the LOM provides the link between small scale experiments, such as AMSA and mini-wash, and the more time consuming full scale experiments in front loader washing machines.

In miniLOM, washes are performed in 50 ml test tubes placed in Stuart rotator.

Enzyme Assays

Assay I

Testing of DNase Activity

DNase activity was determined on DNase Test Agar with Methyl Green (BD, Franklin Lakes, N.J., USA), which was prepared according to the manual from supplier. Briefly, 21 g of agar was dissolved in 500 ml water and then autoclaved for 15 min at 121° C. Autoclaved agar was temperated to 48° C. in water bath, and 20 ml of agar was poured into petri dishes with and allowed to solidify by incubation o/n at room temperature. On solidified agar plates, 5 µl of enzyme solutions are added, and DNase activity are observed as colorless zones around the spotted enzyme solutions.

Assay II
Analysis of E-2-Nonenal on Textile Using an Electronic Nose

One way of testing for the presence of malodor on textiles is by using E-2-Nonenal as a marker for the malodor, as this compound contributes to the malodor on laundry.

Add a solution of E-2-nonenal to a 5 cm×5 cm textile swatch and place the swatch in a 20 mL glass vial for GC analysis and cap the vial. Analyze 5 mL headspace from the capped vials in a Heracles II Electronic nose from Alpha M.O.S., France (double column gas chromatograph with 2 FIDs, column 1: MXT5 and column 2: MXT1701) after 20 minutes incubation at 40° C.

EXAMPLES

Example 1

Preparation of DNA Stained Textile

To prepare DNA stained textile swatches, called "DNA swatches", dissolve DNA in sterile MilliQ water to make a 5.0 mg/mL solution and place in fridge at 5° C. overnight to let the DNA dissolve. Make dilutions of the DNA solution to e.g. 0.5, 1.0 or 2.5 mg/mL in sterile MilliQ water. Place up to 6 circular textile swatches with a 2 cm diameter in a sterile petri dish and apply 100 µL DNA solution of the chosen concentration to each textile swatch and leave them in the petri dish without lid overnight or until dry. To re-apply DNA to washed DNA swatches wait until the washed DNA swatches are dry and apply 100 µL DNA solution of the chosen concentration to each textile swatch and leave them in the petri dish without lid overnight or until dry.

MiniLOM Wash:

Prepare 1 L 15° dH water by pipetting 3.00 mL of 0.713 mol/L CaCl2), 1.50 mL of 0.357 mol/L MgCl2 and 0.3371 g of NaHCO3 into a 1 L measuring cylinder, fill up to 1 L with MilliQ water and stir to dissolve. Weigh of 3.33 g of model detergent A and dissolve in the water. Weigh of 0.70 g Pigment Soil acc. to ILG 09V from wfk Testgewebe GmbH, Germany, and dissolve in the water with detergent, to prepare a dirty detergent solution. Place 5 DNA swatches and 5 clean tracer swatches in each 50 mL plastic beaker (Falcon or NUNC centrifuge tube). Add 10 mL of the dirty detergent solution to each beaker. Put a lid on all the beakers, shake them well to ensure a good distribution of swatches. Mount the beakers in a Mini-Laundr-O-Meter (a Stuart Tube Rotator SB3) and wash at 30° C. for 60 minutes at 20 rpm. After wash the rotator is placed at room temperature while swatches from one beaker at a time are rinsed with 15° dH water and placed back into the rotator. Rinse each beaker 2 times in 20 mL 15° dH water. After the last rinse the swatches are left to dry on filter paper either overnight or until dry (25% relative humidity at 22° C.). If the wash is repeated then reapply DNA to the dry DNA swatches as described above, and perform the wash again also reusing these DNA swatches and the tracer swatches.

Result

This example shows that presence of DNA on textile causes the textile to be static electric after wash when the swatches were dry. The higher a concentration of DNA was placed on the textile before wash the more static electric the swatches were after wash when they were dry. Reapplication of DNA to the DNA swatches before the second wash was done to simulate the swatches getting dirty due to wear between washes.

Preparation of DNA swatches and the MiniLOM washes were done as described above. Deoxyribonucleic acid sodium from Salmon testes D1626 from Sigma Aldrich was used as DNA source. Prewashed (described below) polyester WFK 30A from wfk Testgewebe GmbH, Germany was used as textile. All swatches were at all times handled wearing gloves or using forceps. The experimental setup was made as described in Table 1 below.

Preparation of prewashed textiles in full scale wash: Prewash of textiles are done primarily to remove starch, carboxymethyl cellulose (CMC) and other additives from the textiles. Amylase, cellulase and protease are added to the prewashes to remove these additives which.

The textiles are washed three times in 86.1 g/wash detergent W-ECE-2, from wfk Testgewebe GmbH, Germany using water with 15° dH water hardness (3.00 mL of 0.713 mol/L CaCl2), 1.50 mL of 0.357 mol/L MgCl2 and 0.3371 g of NaHCO3 in 1 L deionized water) and containing the following enzymes:

| Name | g per wash (pre-wash) | | |
|---|---|---|---|
| | Wash 1 | Wash 2 | Wash 3 |
| Savinase 16L | 0.39 | 0 | 0 |
| Stainzyme 12L | 2.6 | 2.6 | 0 |
| Celluclean 5T | 3.25 | 0 | 0 |

The washes are performed in Miele Softtronic W2445 washing machines at 40° C. using a standard wash program with 13-14 liters water to 3 kg textile. After the third wash the textile is dried in a tumble drier

TABLE 1

| Beaker no. | First wash | | Second wash | |
|---|---|---|---|---|
| | DNA swatches | Tracer swatches | DNA reapplied to swatches | Reused tracer swatches |
| 1 | 5 pieces with 5.1 mg/ml DNA | 5 pieces | 5 pieces with 5.1 mg/ml DNA | 5 pieces |
| 2 | 5 pieces with 2.6 mg/ml DNA | 5 pieces | 5 pieces with 2.6 mg/ml DNA | 5 pieces |
| 3 | 5 pieces with 1.0 mg/ml DNA | 5 pieces | 5 pieces with 0.5 mg/ml DNA | 5 pieces |
| 4 | 5 pieces with 0.5 mg/ml DNA | 5 pieces | 5 pieces with 0.26 mg/ml DNA | 5 pieces |
| 5 | 5 pieces with no DNA | 5 pieces | 5 pieces with no DNA | 5 pieces |

After the first wash the swatches were left to dry on filter paper. When dry the swatches were transferred to sterile, polystyrene petri dishes (Nunc™ #254925) and covered with the lid. Surprisingly it was noted that the swatches from beaker 1 to 4 that had previously had DNA applied to them before wash stuck to the lid due to static electricity. The higher the DNA concentration of the swatch the more of the 5 swatches stuck to the lid and the stronger the swatches stuck to the lid. The textile without DNA (beaker 5) did not stick to the lid at all.

DNA was reapplied to the DNA swatches as described above using the DNA concentrations under Second wash in Table 1 above.

After the second wash the swatches were left to dry on filter paper. When dry the swatches were transferred to sterile, polystyrene petri dishes (Nunc™ #254925) and covered with the lid. Again it was noted that the swatches from beaker 1 to 4 that had previously had DNA applied to them before wash stuck to the lid due to static electricity. The higher the DNA concentration of the swatch the more of the 5 swatches stuck to the lid and the stronger the swatches stuck to the lid. Again the textile without DNA (beaker 5) did not stick to the lid at all.

Example 2

Below the invention is illustrated by examples. In the examples below all percentage contents are given in weight. Fabric softening composition A, B and C are prepared with and without DNase added. The DNase (SEQ ID NO: 2) are added in concentrations 0.0004 ppm, 0.004 ppm. 0.04 ppm and 0.5 ppm.

Fabric softening composition A in the form of diluted liquid consist of 7% Esterqut solution, 0.5% silk proteins and 1% perfume composition, and 0.01% colorants. The composition also contains 20 ppm nanoparticles silver preparation with trade name Nano-Silver and water in the amount completing up to 100%. As perfume compositions can be selected from optional perfume products compatible with the composition depending on the concretely made scent. Also the used colorants depend on desired color of the fabric softener.

Fabric softening composition B in the form of concentrate consist of 50% Esterqut solution, 4% cashmere protein and 5% perfume composition, and 0.1% weight colorants. The composition also contains 1000 ppm nanoparticles silver preparation with trade name Nano-Silver and water in the amount completing up to 100%. As perfume compositions can be selected from optional perfume products compatible with the composition depending on the concretely made scent. Also the used colorants depend on desired color of the fabric softener.

Fabric softening composition C in the form of diluted liquid consist of 7% Esterqut solution, 0.5% lanolin and 1% scent/perfume composition and 0.01% colorants. The composition also contains 25 ppm nanoparticles titanium dioxide and water in the amount completing up to 100%. As perfume compositions can be selected from optional perfume products compatible with the composition depending on the concretely made scent. Also the used colorants depend on desired color of the fabric softener.

Example 3

The following are non-limiting examples of the fabric care compositions of the present invention.

| (% wt) | EXAMPLE | | | | | | | | |
|---|---|---|---|---|---|---|---|---|---|
| | I | II | III | IV | V | VI | VII | VIII | IX |
| DHC [a] | 12 | 5 | 4 | 2 | 16.1 | 5 | 5 | | |
| DHC [b] | | 7 | 4 | | | 5 | 5 | 1 | |
| DHC [c] | | | 4 | 10 | | 5 | 5 | | 1 |
| Deposition Aid [d] | 1.25 | 1.25 | 2.00 | 0.75 | 1.44 | 0.42 | 0.25 | 0.5 | 0.70 |
| Perfume | 1.50 | 1.50 | 1.50 | 1.50 | 1.50 | 0.60 | 0.60 | 1.30 | 0.8-1.5 |
| Suds Suppressor [f] | — | — | — | — | — | — | — | — | 0.1 |
| DTPA [g] | 0.005 | 0.005 | 0.005 | 0.005 | 0.007 | 0.002 | 0.002 | 0.20 | — |
| Preservative (ppm) [h] | 5 | 5 | 5 | 5 | 5 | 5 | 5 | — | 250 [i] |
| Antifoam [j] | 0.015 | 0.011 | 0.011 | 0.011 | 0.011 | 0.015 | 0.015 | — | — |
| Dye (ppm) | 40 | 40 | 40 | 40 | 40 | 30 | 30 | 11 | 30-300 |
| Deionized Water | Balance | Balance | Balance | Balance | Balance | Balance | Balance | Balance | Balance |

Fabric softening compositions I to IX are prepared with and without DNase added. The DNase (SEQ ID NO: 2) are added in concentrations 0.0004 ppm, 0.004 ppm. 0.04 ppm and 0.5 ppm.
[a] mono-hydrocarbyl amido quaternary ammonium compound described in claim 1 of WO2011/011247, where the di-hydrocarbyl amido complex having a C12-C14 anionic component and a cationic component having $R_1$ of C16-C18.
[b] mono-hydrocarbyl amido quaternary ammonium compound described in claim 1 of WO2011/011247, where the di-hydrocarbyl amido complex having a C6-C8 anionic component and a cationic component having $R_1$ of C16-C18
[c] mono-hydrocarbyl amido quaternary ammonium compound described in claim 1 of WO2011/011247, where the di-hydrocarbyl amido complex having a C12-C14 anionic component and a cationic component having $R_1$ of C8-C12
[d] Cationic high amylose maize starch available from National Starch under the trade name HYLON VII(R)., Hydrolyzed Cationic Maize Starch, Cationic Waxy Maize starch, US Patent Publ. 2007/0219111A1, paragraph 19.
[f] SE39 from Wacker
[g] Diethylenetriaminepentaacetic acid,
[h] KATHON ®CG available from Rohm and Haas Co. "PPM" is "parts per million."
[i] Gluteraldehyde
[j] Silicone antifoam agent available from Dow Corning Corp. under the trade name DC2310.

Example 4

Pre-Moistened Wipe for Wiping Lenses

A solution comprising water, isopropyl alcohol and sodium laureth sulfate are prepared. DNase (SEQ ID NO: 2) are added in concentrations 0.0004 ppm, 0.004 ppm. 0.04 ppm and 0.5 ppm. A wipe consisting of non-woven textile is dipped in the solution.

The wipe is convenient for cleaning of smudged and greasy lenses. In addition to cleaning the lenses, the wipe removes antistatic charge from the lens. The wipe can be individually packaged and is thereby handy to use. The wipe can be used for eyeglasses, sunglasses, goggles, cell/smartphone screens, computer/laptop screens and more.

The invention claimed is:

1. A method of cleaning a textile, comprising
   (a) washing the textile in a wash liquor, and
   (b) rinsing the textile, wherein a liquid composition comprising a polypeptide having DNase activity is added during rinsing,
wherein static electricity on the textile is prevented, reduced or removed.

2. The method of claim 1, wherein the textile is made of cellulose.

3. The method of claim 1, wherein the textile is made of, cotton, flax/linen, jute, ramie, sisal or coir.

4. The method of claim 1, wherein the textile is made of non-cellulose.

5. The method of claim 1, wherein the textile is made of wool, camel, cashmere, mohair, rabbit or silk.

6. The method of claim 1, wherein the textile is made of polyamide, nylon, aramid, polyester, acrylic, polypropylene or spandex/elastane, or a blend thereof.

7. The method of claim 1, wherein the liquid composition further comprises a surfactant.

8. The method of claim 1, wherein the liquid composition further comprises one or more surfactants, builders, flocculating aid, chelating agents, dye transfer inhibitors, enzyme stabilizers, enzyme inhibitors, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, bacteriocides, fungicides and/or pigments.

9. The method of claim 1, wherein the polypeptide is present in the liquid composition in an amount in the range of 0.00004-100 ppm enzyme protein.

10. The method of claim 1, wherein the polypeptide is present in the liquid composition in an amount in the range of 0.5-10 ppm enzyme protein.

11. The method of claim 1, wherein the liquid composition further comprises a surfactant and a detergent builder in a total concentration of at least 3% by weight.

12. The method of claim 11, wherein the surfactant is an anionic surfactant.

13. The method of claim 1, wherein prior to the washing step, DNA is present on the textile.

* * * * *

SEQUENCE LISTING

<160> NUMBER OF SEQ ID NOS: 8

<210> SEQ ID NO 1
<211> LENGTH: 910
<212> TYPE: DNA
<213> ORGANISM: Aspergillus oryzae
<220> FEATURE:
<221> NAME/KEY: exon
<222> LOCATION: (1)..(242)
<220> FEATURE:
<221> NAME/KEY: Intron
<222> LOCATION: (243)..(308)
<220> FEATURE:
<221> NAME/KEY: exon
<222> LOCATION: (309)..(494)
<220> FEATURE:
<221> NAME/KEY: Intron
<222> LOCATION: (495)..(555)
<220> FEATURE:
<221> NAME/KEY: exon
<222> LOCATION: (556)..(714)
<220> FEATURE:
<221> NAME/KEY: Intron
<222> LOCATION: (715)..(765)
<220> FEATURE:
<221> NAME/KEY: exon
<222> LOCATION: (766)..(907)
<220> FEATURE:
<221> NAME/KEY: Intron
<222> LOCATION: (908)..(910)

<400> SEQUENCE: 1

```
atg cag ctt act aag tcc ctc ctg gta ttc gcg ctt tac atg ttt ggc      48
Met Gln Leu Thr Lys Ser Leu Leu Val Phe Ala Leu Tyr Met Phe Gly
1               5                  10                  15 act cag cac gtt cta gct gtg cct gtc aat ccc gag cct gat gct acg      96
Thr Gln His Val Leu Ala Val Pro Val Asn Pro Glu Pro Asp Ala Thr
            20                  25                  30 agc gtc gaa aat gtt gcc ctt aaa aca ggc agc ggt gat agc cag agc     144
Ser Val Glu Asn Val Ala Leu Lys Thr Gly Ser Gly Asp Ser Gln Ser
        35                  40                  45 gat ccc atc aag gcg gac ttg gag gtc aaa ggc caa agt gct ttg cct     192
Asp Pro Ile Lys Ala Asp Leu Glu Val Lys Gly Gln Ser Ala Leu Pro
    50                  55                  60 ttc gac gtc gac tgc tgg gct atc ctg tgc aag ggc gcc ccg aat gtc     240
Phe Asp Val Asp Cys Trp Ala Ile Leu Cys Lys Gly Ala Pro Asn Val
65                  70                  75                  80 ct    gtatgtcttc ctttattgaa gctcttgatg tggcttgtat gtttgactaa        292
Leu tatatcgcac ccttag g cag cgc gtg aat gaa aag acg aaa aat agt aat     342
                   Gln Arg Val Asn Glu Lys Thr Lys Asn Ser Asn
                                   85                  90 cgc gat cgg agc ggt gcg aac aaa ggg cct ttc aaa gat cct cag aaa     390
Arg Asp Arg Ser Gly Ala Asn Lys Gly Pro Phe Lys Asp Pro Gln Lys
        95                 100                 105 tgg ggc atc aaa gcc ctt cca cct aag aat cca tcc tgg agc gca caa     438
Trp Gly Ile Lys Ala Leu Pro Pro Lys Asn Pro Ser Trp Ser Ala Gln
    110                 115                 120 gac ttc aaa tca ccc gaa gaa tac gca ttt gcg tct tcc ctt caa ggc     486
Asp Phe Lys Ser Pro Glu Glu Tyr Ala Phe Ala Ser Ser Leu Gln Gly
125                 130                 135                 140 gga acc aa   gtatgctaag atcatcactg cttcaatcaa tgtgttgtta            534
Gly Thr Asn gctgactccg atgtgaccaa g t gcc atc cta gcg ccc gtc aac ctc gct tct   586
                        Ala Ile Leu Ala Pro Val Asn Leu Ala Ser
                                145                 150
```

```
cag aac tcc caa ggc ggc gtc ttg aac ggt ttc tac tcg gcg aac aaa        634
Gln Asn Ser Gln Gly Gly Val Leu Asn Gly Phe Tyr Ser Ala Asn Lys
        155                 160                 165 gta gca caa ttt gat cct agc aag ccc caa cag aca aag gga aca tgg        682
Val Ala Gln Phe Asp Pro Ser Lys Pro Gln Gln Thr Lys Gly Thr Trp
170                 175                 180                 185 ttt cag atc act aag ttc aca ggt gca gct gg gtaagaactt ccagtaccat       734
Phe Gln Ile Thr Lys Phe Thr Gly Ala Ala Gly
                190                 195 ggtcatatgc aatttactaa gaaaatacta g t cct tac tgc aag gct ctg ggg       787
                                  Pro Tyr Cys Lys Ala Leu Gly
                                                      200 agt aat gat aag agt gtg tgc gat aag aac aag aat att gca ggg gac        835
Ser Asn Asp Lys Ser Val Cys Asp Lys Asn Lys Asn Ile Ala Gly Asp
        205                 210                 215 tgg ggc ttc gac ccg gcg aaa tgg gca tat cag tat gat gag aag aat        883
Trp Gly Phe Asp Pro Ala Lys Trp Ala Tyr Gln Tyr Asp Glu Lys Asn
220                 225                 230                 235 aac aag ttc aac tat gtt ggt aag taa                                    910
Asn Lys Phe Asn Tyr Val Gly Lys
                240

<210> SEQ ID NO 2
<211> LENGTH: 243
<212> TYPE: PRT
<213> ORGANISM: Aspergillus oryzae
<220> FEATURE:
<221> NAME/KEY: SIGNAL
<222> LOCATION: (1)..(22)
<220> FEATURE:
<221> NAME/KEY: PROPEP
<222> LOCATION: (23)..(37)
<220> FEATURE:
<221> NAME/KEY: PEPTIDE
<222> LOCATION: (38)..(243)

<400> SEQUENCE: 2

Met Gln Leu Thr Lys Ser Leu Leu Val Phe Ala Leu Tyr Met Phe Gly
1               5                   10                  15

Thr Gln His Val Leu Ala Val Pro Val Asn Pro Glu Pro Asp Ala Thr
            20                  25                  30

Ser Val Glu Asn Val Ala Leu Lys Thr Gly Ser Gly Asp Ser Gln Ser
        35                  40                  45

Asp Pro Ile Lys Ala Asp Leu Glu Val Lys Gly Gln Ser Ala Leu Pro
    50                  55                  60

Phe Asp Val Asp Cys Trp Ala Ile Leu Cys Lys Gly Ala Pro Asn Val
65                  70                  75                  80

Leu Gln Arg Val Asn Glu Lys Thr Lys Asn Ser Asn Arg Asp Arg Ser
                85                  90                  95

Gly Ala Asn Lys Gly Pro Phe Lys Asp Pro Gln Lys Trp Gly Ile Lys
            100                 105                 110

Ala Leu Pro Pro Lys Asn Pro Ser Trp Ser Ala Gln Asp Phe Lys Ser
        115                 120                 125

Pro Glu Glu Tyr Ala Phe Ala Ser Ser Leu Gln Gly Gly Thr Asn Ala
    130                 135                 140

Ile Leu Ala Pro Val Asn Leu Ala Ser Gln Asn Ser Gln Gly Gly Val
145                 150                 155                 160

Leu Asn Gly Phe Tyr Ser Ala Asn Lys Val Ala Gln Phe Asp Pro Ser
                165                 170                 175
```

```
Lys Pro Gln Gln Thr Lys Gly Thr Trp Phe Gln Ile Thr Lys Phe Thr
            180                 185                 190

Gly Ala Ala Gly Pro Tyr Cys Lys Ala Leu Gly Ser Asn Asp Lys Ser
        195                 200                 205

Val Cys Asp Lys Asn Lys Asn Ile Ala Gly Asp Trp Gly Phe Asp Pro
    210                 215                 220

Ala Lys Trp Ala Tyr Gln Tyr Asp Glu Lys Asn Asn Lys Phe Asn Tyr
225                 230                 235                 240

Val Gly Lys

<210> SEQ ID NO 3
<211> LENGTH: 204
<212> TYPE: PRT
<213> ORGANISM: Aspergillus oryzae
<220> FEATURE:
<221> NAME/KEY: PEPTIDE
<222> LOCATION: (1)..(204)

<400> SEQUENCE: 3

Lys Thr Gly Ser Gly Asp Ser Gln Ser Asp Pro Ile Lys Ala Asp Leu
1               5                   10                  15

Glu Val Lys Gly Gln Ser Ala Leu Pro Phe Asp Val Asp Cys Trp Ala
            20                  25                  30

Ile Leu Cys Lys Gly Ala Pro Asn Val Leu Gln Arg Val Asn Glu Lys
        35                  40                  45

Thr Lys Asn Ser Asn Arg Asp Arg Ser Gly Ala Asn Lys Gly Pro Phe
    50                  55                  60

Lys Asp Pro Gln Lys Trp Gly Ile Lys Ala Leu Pro Pro Lys Asn Pro
65                  70                  75                  80

Ser Trp Ser Ala Gln Asp Phe Lys Ser Pro Glu Glu Tyr Ala Phe Ala
                85                  90                  95

Ser Ser Leu Gln Gly Gly Thr Asn Ala Ile Leu Ala Pro Val Asn Leu
            100                 105                 110

Ala Ser Gln Asn Ser Gln Gly Gly Val Leu Asn Gly Phe Tyr Ser Ala
        115                 120                 125

Asn Lys Val Ala Gln Phe Asp Pro Ser Lys Pro Gln Gln Thr Lys Gly
    130                 135                 140

Thr Trp Phe Gln Ile Thr Lys Phe Thr Gly Ala Ala Gly Pro Tyr Cys
145                 150                 155                 160

Lys Ala Leu Gly Ser Asn Asp Lys Ser Val Cys Asp Lys Asn Lys Asn
                165                 170                 175

Ile Ala Gly Asp Trp Gly Phe Asp Pro Ala Lys Trp Ala Tyr Gln Tyr
            180                 185                 190

Asp Glu Lys Asn Asn Lys Phe Asn Tyr Val Gly Lys
        195                 200

<210> SEQ ID NO 4
<211> LENGTH: 868
<212> TYPE: DNA
<213> ORGANISM: Trichoderma harzianum
<220> FEATURE:
<221> NAME/KEY: exon
<222> LOCATION: (1)..(75)
<220> FEATURE:
<221> NAME/KEY: Intron
<222> LOCATION: (76)..(154)
<220> FEATURE:
<221> NAME/KEY: exon
<222> LOCATION: (155)..(288)
<220> FEATURE:
```

```
<221> NAME/KEY: Intron
<222> LOCATION: (289)..(362)
<220> FEATURE:
<221> NAME/KEY: exon
<222> LOCATION: (363)..(519)
<220> FEATURE:
<221> NAME/KEY: Intron
<222> LOCATION: (520)..(615)
<220> FEATURE:
<221> NAME/KEY: exon
<222> LOCATION: (616)..(867)

<400> SEQUENCE: 4
```

| | | |
|---|---|---|
| atg aag ctg tcc atc tct gtc gct ctt act tcg gcc atc gcg gtt ctc<br>Met Lys Leu Ser Ile Ser Val Ala Leu Thr Ser Ala Ile Ala Val Leu<br>1                  5                    10                15 | | 48 |
| gcc gcc ccg gct cct atg cct aca ccg gtatgtagca tcaatgcaac<br>Ala Ala Pro Ala Pro Met Pro Thr Pro<br>                20                    25 | | 95 |
| atgacataac ttgtatctcg actatatatc agactggcta atgcttcaac tcattacag | | 154 |
| ccc ggt att ccc acg gaa agc agc gcc aga acc caa ctt gcc ggc ctg<br>Pro Gly Ile Pro Thr Glu Ser Ser Ala Arg Thr Gln Leu Ala Gly Leu<br>                      30                    35                    40 | | 202 |
| act gtt gcc gtt gct ggc tct gga act ggt tac tcc cgc gac ctg ttt<br>Thr Val Ala Val Ala Gly Ser Gly Thr Gly Tyr Ser Arg Asp Leu Phe<br>                      45                    50                    55 | | 250 |
| ccc act tgg gat gcc atc tct ggt aac tgc aac gct cg gtatgataac<br>Pro Thr Trp Asp Ala Ile Ser Gly Asn Cys Asn Ala Arg<br>                  60                    65                    70 | | 298 |
| atcctaggac ctttcaagct tcggaaatac aacacaaagg ctaacaaagt ggatgtgcaa | | 358 |
| atag c gaa tat gtg ttg aag cga gat ggt gaa ggt gtc caa gtc aac<br>       Glu Tyr Val Leu Lys Arg Asp Gly Glu Gly Val Gln Val Asn<br>                                75                    80 | | 405 |
| aat gct tgt gaa tct cag tcc ggc acc tgg atc aga tcc tta tga caa<br>Asn Ala Cys Glu Ser Gln Ser Gly Thr Trp Ile Arg Ser Leu     Gln<br>85                    90                    95 | | 453 |
| cgc cag ttt cac aaa tgc atc cag ctt gga tat tga cca cat ggt gcc<br>Arg Gln Phe His Lys Cys Ile Gln Leu Gly Tyr     Pro His Gly Ala<br>100                  105                  110 | | 501 |
| tct aaa gaa tgc ctg gat cgtgagtttt ctcctttttc actgcgtatc<br>Ser Lys Glu Cys Leu Asp<br>115                  120 | | 549 |
| tccgttccct acctttttgc gatactatat catgccacat cactaatatg gacaaatttc | | 609 |
| tcgcca gtc cgg tgc ctc aag ctg gac cac agc cca acg tga agc cct<br>       Val Arg Cys Leu Lys Leu Asp His Ser Pro Thr     Ser Pro<br>                              125                         130 | | 657 |
| cgc caa cga cgt ctc ccg tcc cca act ctg ggc cgt ctc cgc aag cgc<br>Arg Gln Arg Arg Leu Pro Ser Pro Thr Leu Gly Arg Leu Arg Lys Arg<br>               135                    140                    145 | | 705 |
| aaa ccg ctc caa ggg cga ccg cag ccc aga cca gtg gaa gcc tcc tct<br>Lys Pro Leu Gln Gly Arg Pro Gln Pro Arg Pro Val Glu Ala Ser Ser<br>150                  155                    160                    165 | | 753 |
| gac cag ctt cta ctg cac cta cgc caa gtc gtg gat cga tgt caa gag<br>Asp Gln Leu Leu Leu His Leu Arg Gln Val Val Asp Arg Cys Gln Glu<br>                      170                    175                    180 | | 801 |
| ctt cta taa gct gac aat cac cag tgc cga gaa gac agc tct gag cag<br>Leu Leu     Ala Asp Asn His Gln Cys Arg Glu Asp Ser Ser Glu Gln<br>                                185                    190                    195 | | 849 |
| cat gtt aga tac ttg cta g<br>His Val Arg Tyr Leu Leu<br>                200 | | 868 |

<210> SEQ ID NO 5
<211> LENGTH: 205
<212> TYPE: PRT
<213> ORGANISM: Trichoderma harzianum
<220> FEATURE:
<221> NAME/KEY: SIGNAL
<222> LOCATION: (1)..(17)
<220> FEATURE:
<221> NAME/KEY: PEPTIDE
<222> LOCATION: (18)..(205)

<400> SEQUENCE: 5

Met Lys Leu Ser Ile Ser Val Ala Leu Thr Ser Ala Ile Ala Val Leu
1               5                   10                  15

Ala Ala Pro Ala Pro Met Pro Thr Pro Pro Gly Ile Pro Thr Glu Ser
            20                  25                  30

Ser Ala Arg Thr Gln Leu Ala Gly Leu Thr Val Ala Val Ala Gly Ser
        35                  40                  45

Gly Thr Gly Tyr Ser Arg Asp Leu Phe Pro Thr Trp Asp Ala Ile Ser
    50                  55                  60

Gly Asn Cys Asn Ala Arg Glu Tyr Val Leu Lys Arg Asp Gly Glu Gly
65                  70                  75                  80

Val Gln Val Asn Asn Ala Cys Glu Ser Gln Ser Gly Thr Trp Ile Ser
                85                  90                  95

Pro Tyr Asp Asn Ala Ser Phe Thr Asn Ala Ser Ser Leu Asp Ile Asp
            100                 105                 110

His Met Val Pro Leu Lys Asn Ala Trp Ile Ser Gly Ala Ser Ser Trp
        115                 120                 125

Thr Thr Ala Gln Arg Glu Ala Leu Ala Asn Asp Val Ser Arg Pro Gln
    130                 135                 140

Leu Trp Ala Val Ser Ala Ser Ala Asn Arg Ser Lys Gly Asp Arg Ser
145                 150                 155                 160

Pro Asp Gln Trp Lys Pro Pro Leu Thr Ser Phe Tyr Cys Thr Tyr Ala
                165                 170                 175

Lys Ser Trp Ile Asp Val Lys Ser Phe Tyr Lys Leu Thr Ile Thr Ser
            180                 185                 190

Ala Glu Lys Thr Ala Leu Ser Ser Met Leu Asp Thr Cys
        195                 200                 205

<210> SEQ ID NO 6
<211> LENGTH: 136
<212> TYPE: PRT
<213> ORGANISM: Bacillus subtilis
<220> FEATURE:
<221> NAME/KEY: SIGNAL
<222> LOCATION: (1)..(26)
<220> FEATURE:
<221> NAME/KEY: PEPTIDE
<222> LOCATION: (27)..(136)

<400> SEQUENCE: 6

Met Lys Lys Trp Met Ala Gly Leu Phe Leu Ala Ala Val Leu Leu
1               5                   10                  15

Cys Leu Met Val Pro Gln Gln Ile Gln Gly Ala Ser Ser Tyr Asp Lys
            20                  25                  30

Val Leu Tyr Phe Pro Leu Ser Arg Tyr Pro Glu Thr Gly Ser His Ile
        35                  40                  45

Arg Asp Ala Ile Ala Glu Gly His Pro Asp Ile Cys Thr Ile Asp Arg
    50                  55                  60

-continued

Asp Gly Ala Asp Lys Arg Arg Glu Glu Ser Leu Lys Gly Ile Pro Thr
65                  70                  75                  80

Lys Pro Gly Tyr Asp Arg Asp Glu Trp Pro Met Ala Val Cys Glu Glu
            85                  90                  95

Gly Gly Ala Gly Ala Asp Val Arg Tyr Val Thr Pro Ser Asp Asn Arg
        100                 105                 110

Gly Ala Gly Ser Trp Val Gly Asn Gln Met Ser Ser Tyr Pro Asp Gly
    115                 120                 125

Thr Arg Val Leu Phe Ile Val Gln
    130                 135

<210> SEQ ID NO 7
<211> LENGTH: 142
<212> TYPE: PRT
<213> ORGANISM: Bacillus licheniformis
<220> FEATURE:
<221> NAME/KEY: SIGNAL
<222> LOCATION: (1)..(33)
<220> FEATURE:
<221> NAME/KEY: PEPTIDE
<222> LOCATION: (34)..(136)

<400> SEQUENCE: 7

Met Ile Lys Lys Trp Ala Val His Leu Leu Phe Ser Ala Leu Val Leu
1               5                   10                  15

Leu Gly Leu Ser Gly Gly Ala Ala Tyr Ser Pro Gln His Ala Glu Gly
            20                  25                  30

Ala Ala Arg Tyr Asp Asp Ile Leu Tyr Phe Pro Ala Ser Arg Tyr Pro
        35                  40                  45

Glu Thr Gly Ala His Ile Ser Asp Ala Ile Lys Ala Gly His Ser Asp
    50                  55                  60

Val Cys Thr Ile Glu Arg Ser Gly Ala Asp Lys Arg Arg Gln Glu Ser
65                  70                  75                  80

Leu Lys Gly Ile Pro Thr Lys Pro Gly Phe Asp Arg Asp Glu Trp Pro
            85                  90                  95

Met Ala Met Cys Glu Glu Gly Gly Lys Gly Ala Ser Val Arg Tyr Val
        100                 105                 110

Ser Ser Ser Asp Asn Arg Gly Ala Gly Ser Trp Val Gly Asn Arg Leu
    115                 120                 125

Ser Gly Phe Ala Asp Gly Thr Arg Ile Leu Phe Ile Val Gln
    130                 135                 140

<210> SEQ ID NO 8
<211> LENGTH: 206
<212> TYPE: PRT
<213> ORGANISM: Aspergillus oryzae

<400> SEQUENCE: 8

Ala Leu Lys Thr Gly Ser Gly Asp Ser Gln Ser Asp Pro Ile Lys Ala
1               5                   10                  15

Asp Leu Glu Val Lys Gly Gln Ser Ala Leu Pro Phe Asp Val Asp Cys
            20                  25                  30

Trp Ala Ile Leu Cys Lys Gly Ala Pro Asn Val Leu Gln Arg Val Asn
        35                  40                  45

Glu Lys Thr Lys Asn Ser Asn Arg Asp Arg Ser Gly Ala Asn Lys Gly
    50                  55                  60

Pro Phe Lys Asp Pro Gln Lys Trp Gly Ile Lys Ala Leu Pro Pro Lys
65                  70                  75                  80

-continued

```
Asn Pro Ser Trp Ser Ala Gln Asp Phe Lys Ser Pro Glu Glu Tyr Ala
            85                  90                  95
Phe Ala Ser Ser Leu Gln Gly Gly Thr Asn Ala Ile Leu Ala Pro Val
            100             105                 110
Asn Leu Ala Ser Gln Asn Ser Gln Gly Gly Val Leu Asn Gly Phe Tyr
        115             120                 125
Ser Ala Asn Lys Val Ala Gln Phe Asp Pro Ser Lys Pro Gln Gln Thr
        130             135             140
Lys Gly Thr Trp Phe Gln Ile Thr Lys Phe Thr Gly Ala Ala Gly Pro
145             150             155                 160
Tyr Cys Lys Ala Leu Gly Ser Asn Asp Lys Ser Val Cys Asp Lys Asn
                165             170             175
Lys Asn Ile Ala Gly Asp Trp Gly Phe Asp Pro Ala Lys Trp Ala Tyr
            180             185                 190
Gln Tyr Asp Glu Lys Asn Asn Lys Phe Asn Tyr Val Gly Lys
        195             200             205
```